US012688273B1

(12) United States Patent　　　(10) Patent No.: US 12,688,273 B1
Townsend, III et al.　　　　　　　(45) Date of Patent: Jul. 21, 2026

(54) METHODS AND SYSTEMS FOR CHARGING AND MONITORING ELECTRONIC DEVICES IN CONFINEMENT INSTITUTIONS

(71) Applicant: CONFINEMENT TELEPHONY TECHNOLOGY, LLC, Greensboro, NC (US)

(72) Inventors: John Vincent Townsend, III, Kernersville, NC (US); Rick Allen Lubbehusen, Winston-Salem, NC (US); Jeffrey Adam Livaudais, Summerfield, NC (US); Timothy Edwin Pabon, Greensboro, NC (US); Johnnie Richard Tayloe, Rural Hall, NC (US); Nathan Robert Fisher, Hickory, NC (US); John Kyle Townsend, Kernersville, NC (US); Franklin Wayne Harrelson, Jr., Greensboro, NC (US)

(73) Assignee: CONFINEMENT TELEPHONY TECHNOLOGY, LLC, Greensboro, NC (US)

( * ) Notice: Subject to any disclaimer, the term of this patent is extended or adjusted under 35 U.S.C. 154(b) by 0 days.

(21) Appl. No.: 19/411,941

(22) Filed: Dec. 8, 2025

Related U.S. Application Data

(60) Continuation-in-part of application No. 18/133,002, filed on Apr. 11, 2023, now Pat. No. 12,566,834,
(Continued)

(51) Int. Cl.
　　*G06F 21/35*　　　(2013.01)
　　*A61L 2/10*　　　(2026.01)
　　(Continued)

(52) U.S. Cl.
　　CPC ................ *G06F 21/35* (2013.01); *A61L 2/10* (2013.01); *A61L 2/24* (2013.01); *G06V 40/166* (2022.01);
(Continued)

(58) Field of Classification Search
None
See application file for complete search history.

(56) References Cited

U.S. PATENT DOCUMENTS 5,303,214　A　*　4/1994　Kulakowski ......... G11B 17/225
10,574,005　B1 *　2/2020　Baldwin ............... H01R 27/02
(Continued)

FOREIGN PATENT DOCUMENTS

CN　　　203205893 U　　9/2013
CN　　　103826906 B　　5/2014
(Continued)

OTHER PUBLICATIONS

US Patent and Trademark Office, Notice of Allowance, U.S. Appl. No. 18/133,002, 9 pages, Aug. 27, 2025.
(Continued)

*Primary Examiner* — Mohammed Rachedine
(74) *Attorney, Agent, or Firm* — Thompson Hine LLP

(57)　　　　　ABSTRACT

Implementations disclosed herein provide a charging station configured to attach to or be positioned adjacent to a wall in a confinement institution and to simultaneously charge multiple tablets, mobile phones, laptops, or other portable electronic devices. In some implementations, the charging station is configured with protective sides that may help protect inserted electronic devices from damage. The charging and use of the electronic devices within the confinement institution may be automatically managed based on connections at the charging stations, communications with the electronic devices, audio, images, or video of the electronic devices or (Continued)

Identify a charging station event at a charging station ⟋ 10

Identify the electronic device involved in the charging station event ⟋ 20

Identify the user involved in the charging station event ⟋ 30

Track use of the electronic device based on identifying the mobile device and the user involved in the charging station event ⟋ 40 users captured cameras on the charging station or the electronic devices, and/or information provided by the users.

13 Claims, 14 Drawing Sheets

Related U.S. Application Data which is a continuation-in-part of application No. 17/215,757, filed on Mar. 29, 2021, now Pat. No. 11,658,496, which is a division of application No. 16/429,698, filed on Jun. 3, 2019, now Pat. No. 11,050,278, said application No. 18/133,002 is a continuation-in-part of application No. 17/215,833, filed on Mar. 29, 2021, now Pat. No. 11,658,497, which is a division of application No. 16/429,698, filed on Jun. 3, 2019, now Pat. No. 11,050,278.

(60) Provisional application No. 62/682,241, filed on Jun. 8, 2018.

(51) Int. Cl.

| | |
|---|---|
| *A61L 2/24* | (2006.01) |
| *G06V 40/16* | (2022.01) |
| *G10L 17/00* | (2013.01) |
| *H02J 7/47* | (2026.01) |
| *H02J 7/70* | (2026.01) |
| *H02J 7/80* | (2026.01) |

(52) U.S. Cl.
CPC ............ *G06V 40/172* (2022.01); *G10L 17/00* (2013.01); *H02J 7/47* (2026.01); *H02J 7/751* (2026.01); *H02J 7/80* (2026.01); *A61L 2202/11* (2013.01)

(56) References Cited

U.S. PATENT DOCUMENTS

| | | | | |
|---|---|---|---|---|
| 10,624,241 B1 * | 4/2020 | Ross | ................. | H05K 7/20736 |
| 10,742,046 B2 * | 8/2020 | Baldasare | ............ | H04W 4/023 |
| 11,349,951 B1 * | 5/2022 | Noland | ................... | H04L 67/14 |
| 2004/0033478 A1 * | 2/2004 | Knowles | .............. | H04M 1/725 |
| | | | | 434/350 |
| 2012/0105197 A1 | 5/2012 | Kobres | | |
| 2013/0175993 A1 * | 7/2013 | Chen | ..................... | H02J 7/731 |
| | | | | 320/114 |
| 2016/0188933 A1 | 6/2016 | Powell | | |
| 2016/0342874 A1 | 11/2016 | Powell | | |
| 2016/0352118 A1 * | 12/2016 | Huang | ...................... | H02J 7/70 |
| 2016/0375783 A1 | 12/2016 | Uyeki | | |
| 2017/0004340 A1 | 1/2017 | Powell | | |
| 2017/0256051 A1 | 9/2017 | Dwivedi | | |
| 2018/0224620 A1 * | 8/2018 | Ebrahimi | .......... | G02B 6/44528 |
| 2018/0351375 A1 | 12/2018 | Baldasare | | |

FOREIGN PATENT DOCUMENTS

| | | | | | |
|---|---|---|---|---|---|
| CN | 107026492 | A | | 8/2017 | |
| CN | 206380961 | U | * | 8/2017 | |
| CN | 107668978 | A | * | 2/2018 | ............ A47B 97/00 |
| CN | 206961247 | U | | 2/2018 | |
| CN | 207917437 | U | * | 9/2018 | |
| CN | 208433768 | U | * | 1/2019 | |
| CN | 210743087 | U | | 6/2020 | |
| TW | 201909095 | A | | 3/2019 | |

OTHER PUBLICATIONS

US Patent and Trademark Office, Non-Final Office Action, U.S. Appl. No. 17/215,757, 16 pages, Oct. 5, 2022.
US Patent and Trademark Office, Notice of Allowance, U.S. Appl. No. 17/215,757, 8 pages, Feb. 9, 2023.
US Patent and Trademark Office, Non-Final Office Action, U.S. Appl. No. 17/215,833, 15 pages, Sep. 26, 2022.
US Patent and Trademark Office, Notice of Allowance, U.S. Appl. No. 17/215,833, 8 pages, Jan. 20, 2023.

* cited by examiner

5

Identify a charging station event at a charging station ⟋ 10

Identify the electronic device involved
in the charging station event ⟋ 20

Identify the user involved in the
charging station event ⟋ 30

Track use of the electronic device based on
identifying the mobile device and the user involved in
the charging station event ⟋ 40

50

Management
Unit
200

CPU(s)
502

Comm.
Interface(s)
508

Memory 520

Operating System 530

Application(s) 540

Device Management Unit 542

Database 550

Data 552

504

Programming
Interface(s)
510

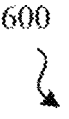
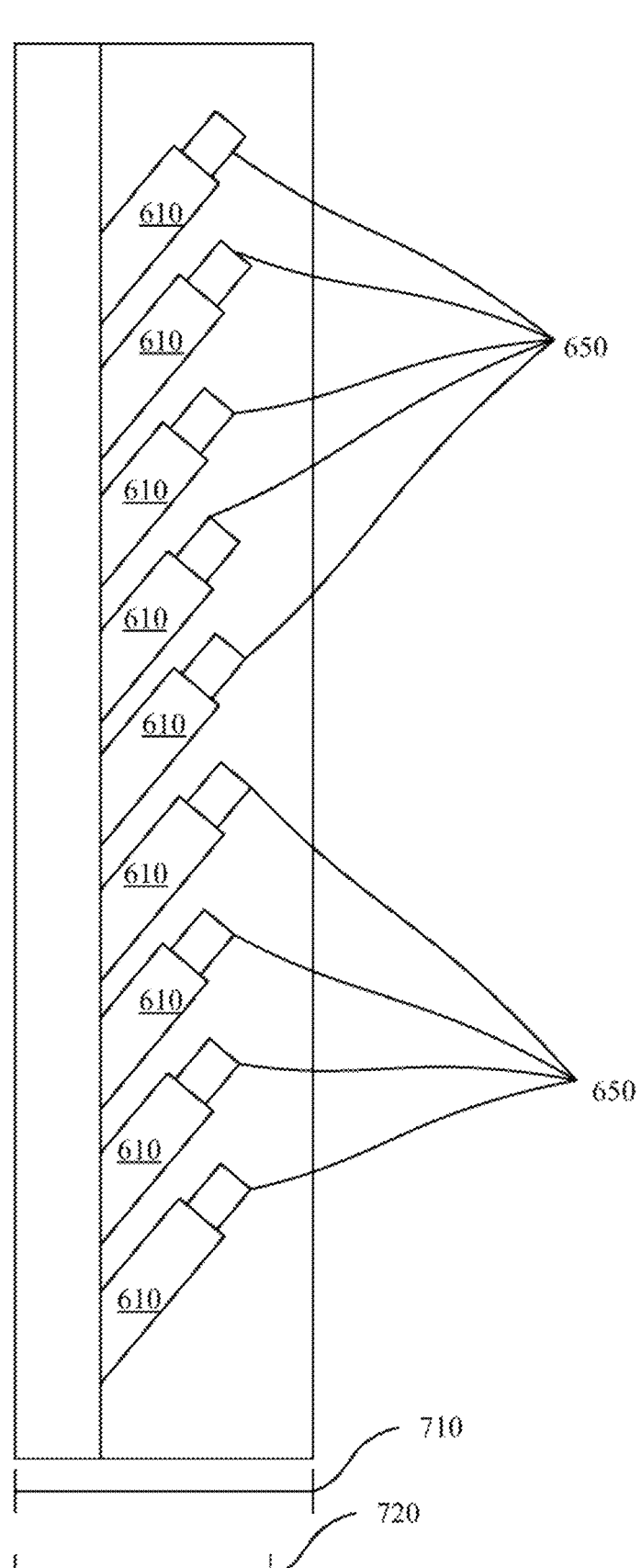
FIG. 7

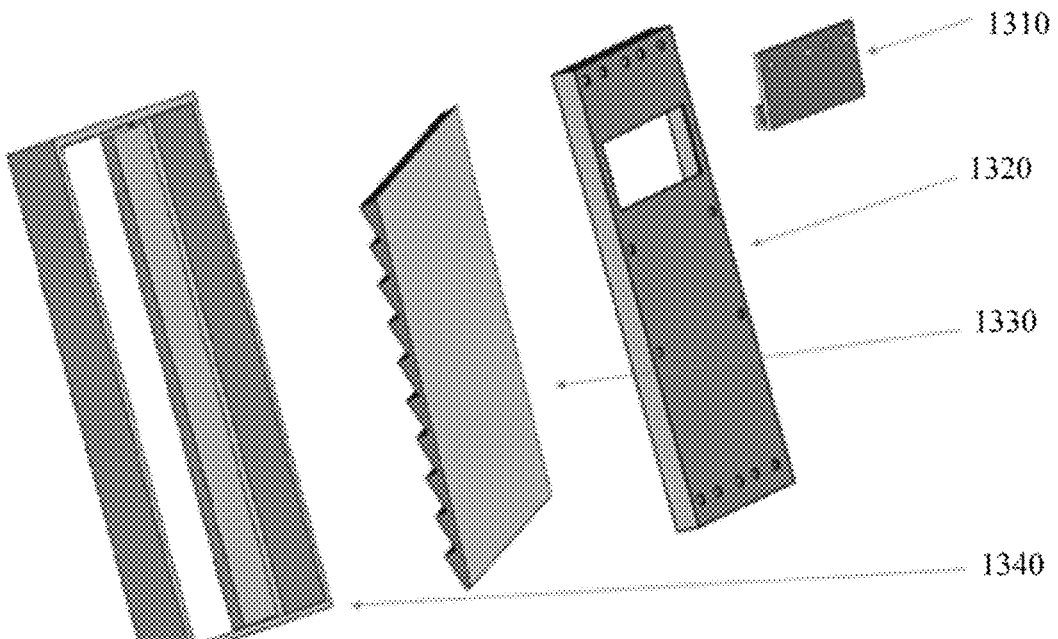
FIG. 9
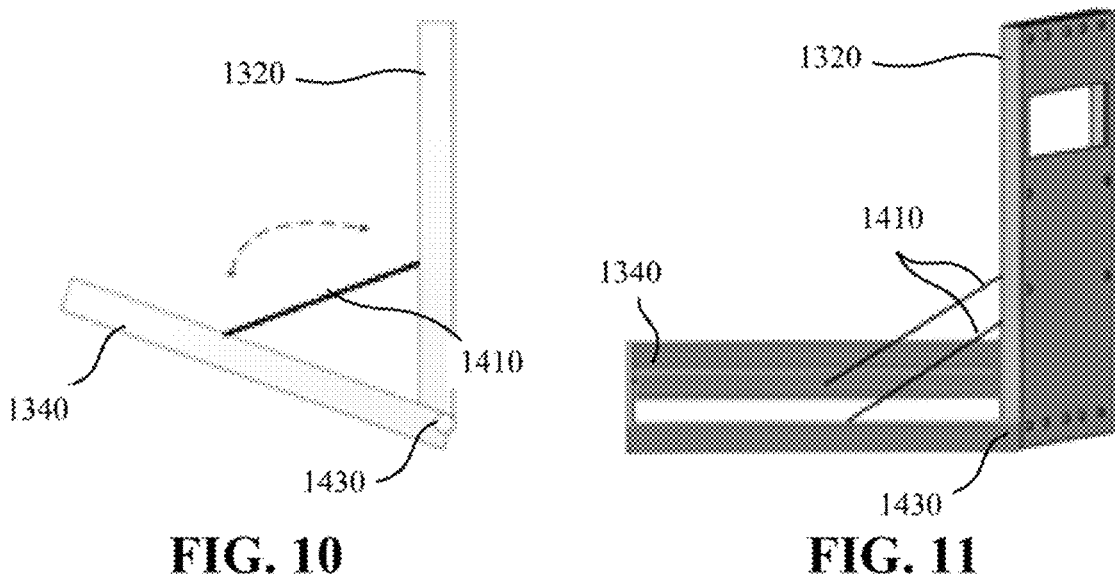
FIG. 10          FIG. 11

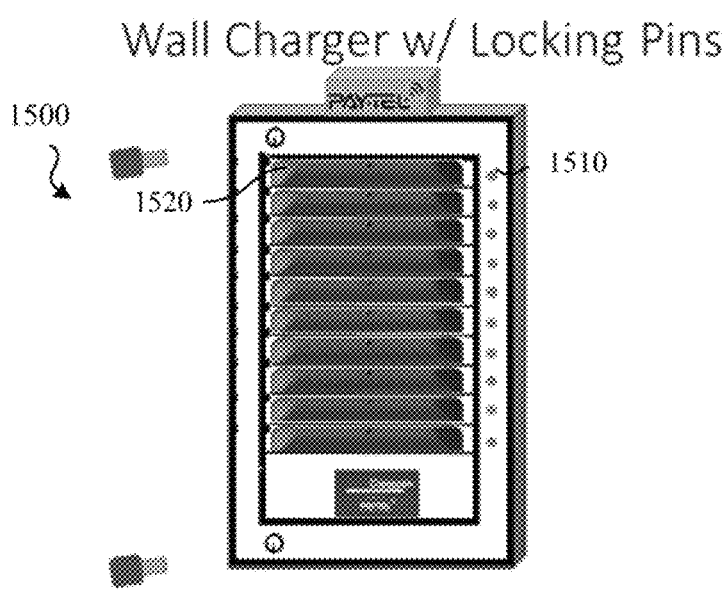
1500
1520
1510
Wall Charger w/ Locking Pins
FIG. 15A
SIDE VIEW of Unit
1510
1520
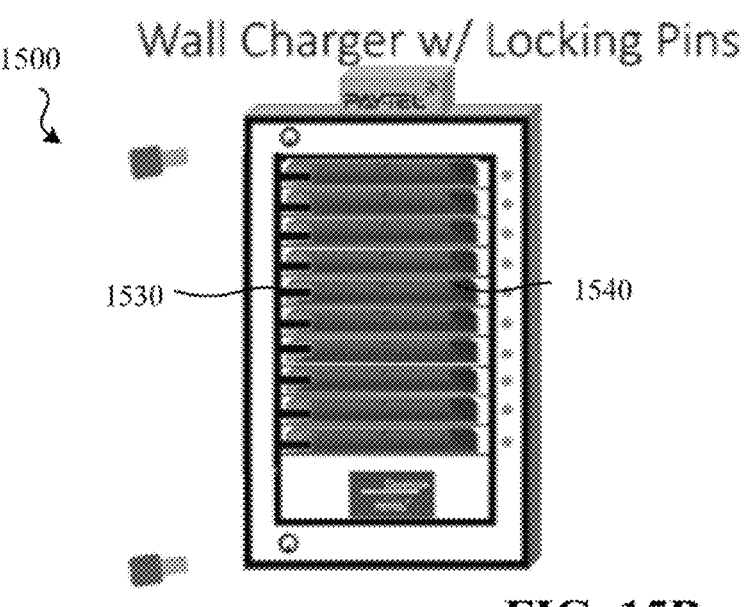
1500
1530
1540
Wall Charger w/ Locking Pins
FIG. 15B
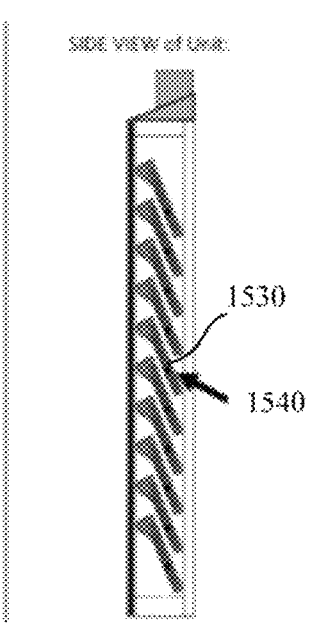
SIDE VIEW of Unit
1530
1540

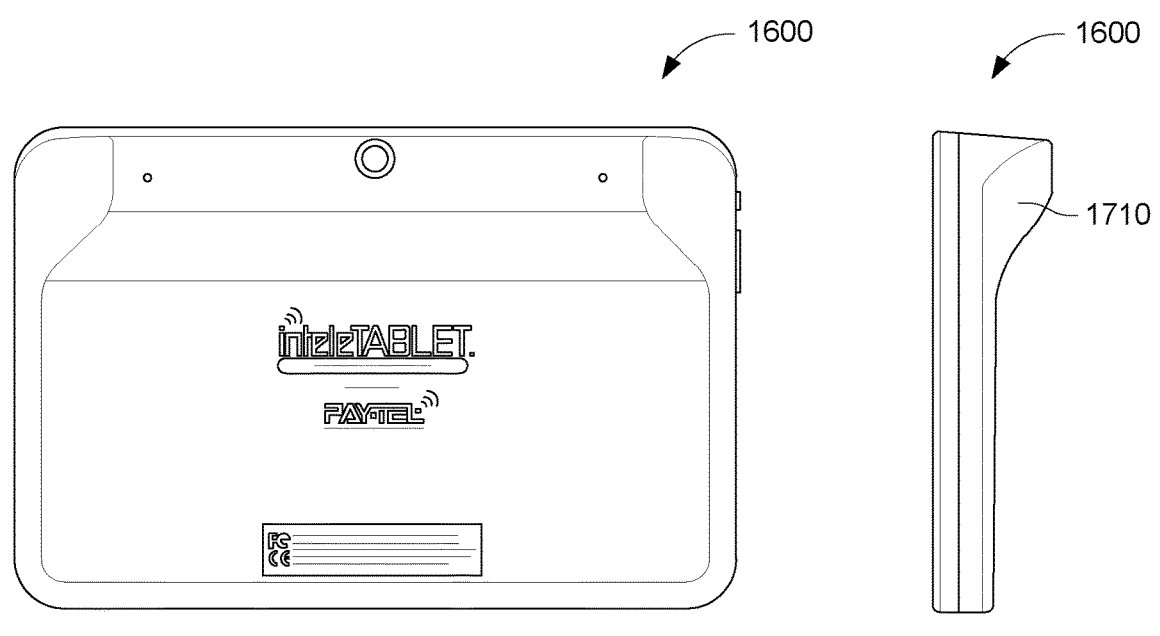
FIG. 16                    FIG. 17
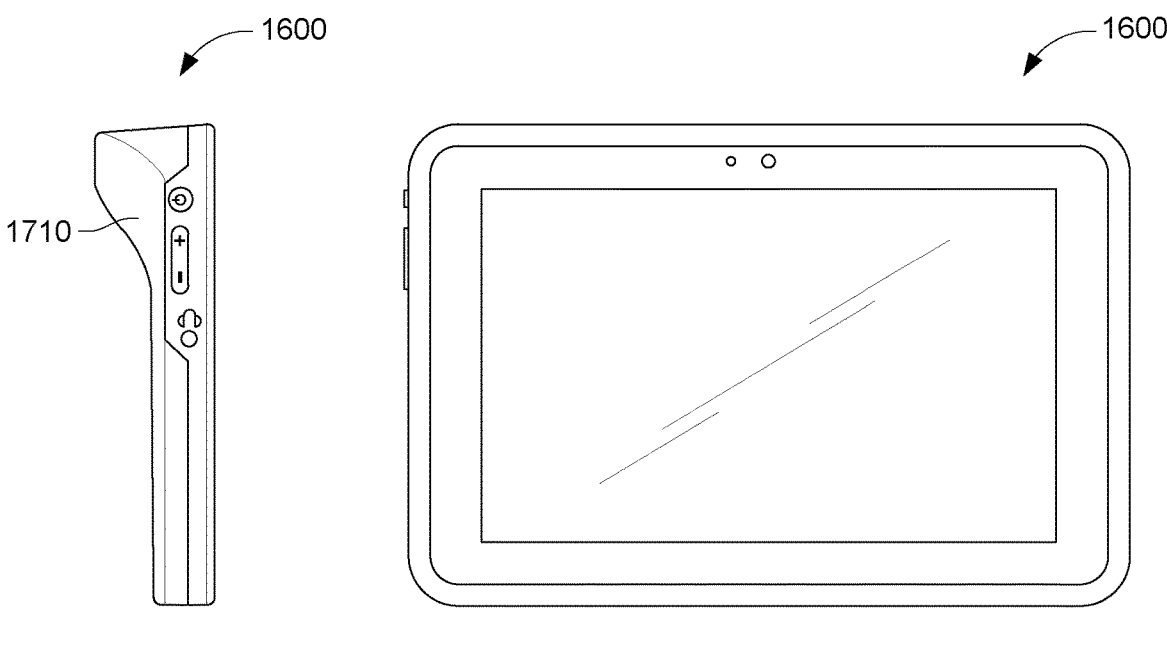
FIG. 18                    FIG. 19

METHODS AND SYSTEMS FOR CHARGING AND MONITORING ELECTRONIC DEVICES IN CONFINEMENT INSTITUTIONS

CROSS-REFERENCE TO RELATED APPLICATION

This Application is a continuation-in-part of U.S. patent application Ser. No. 18/133,002 filed on Apr. 11, 2023, which is a continuation-in-part of U.S. patent application Ser. No. 17/215,757 filed on Mar. 29, 2021 (now U.S. Pat. No. 11,658,496), and a continuation-in-part of U.S. patent application Ser. No. 17/215,833 filed on Mar. 29, 2021 (now U.S. Pat. No. 11,658,497), both of which are divisional applications of U.S. patent application Ser. No. 16/429,698 filed on Jun. 3, 2019 (now U.S. Pat. No. 11,050,278), which claims the benefit of U.S. Provisional Application No. 62/682,241 filed Jun. 8, 2018, each of which is incorporated herein by this reference in its entirety.

FIELD OF THE INVENTION

This disclosure relates generally to electronic devices, systems, and methods used in confinement institutions, including devices, systems, and methods that are used to charge tablets and other electronic devices and perform various other useful functions in confinement institutions.

BACKGROUND

Confinement institution inmates have traditionally had very limited access to telephones and other electronic devices. Recently, confinement institutions have begun allowing inmates to use tablets and other mobile electronic devices. Charging such devices presents numerous challenges in the context of confinement institutions, and existing cord-based and cart-based charging systems generally do not adequately account for inmate safety, space limitations, security, and other concerns in these environments. The dispersion and collection of electronic devices within confinement institutions also presents challenges. Officers of the institution may be able to assist with dispersion and collection of electronic devices in some circumstances. However, the availability of officers to do so is generally limited significantly by the demands on the time of the officers for other duties. It is also generally desirable to avoid accessories (e.g., wires, USB storage devices, etc.) and the use of cords as such accessories and cords may increase the time and effort required to address the charging, dispersion, and collection of devices in confinement institutions. In addition, various safety risks are associated with cords.

SUMMARY

As described above, existing cord-based and cart-based charging systems generally do not adequately account for inmate safety, space limitations, security, and other concerns. Implementations disclosed herein provide a charging station configured to attach to or be positioned adjacent to a wall or bars in a confinement institution and to simultaneously charge multiple tablets, mobile phones, laptops, or other portable electronic devices. The charging station can be configured with a slim profile, for example, in some implementations extending from the wall less than 6 inches, less than 12 inches, less than 18 inches, or less than 24 inches. Such a slim profile may be less likely to interfere with doors, corridor traffic, and room usage and may make the charging station less likely to be damaged. In some implementations, a slim profile charging station is configured to use significantly less space that a cart-based or box charger and is suitable for installation in narrow hallways and rooms with various space constraints.

In some implementations, a charging station is configured with protective sides that may help protect inserted electronic devices (e.g., tablets) from damage. For example, a charging station may include a rack that includes a back and one or more structures that form a row of slots extending a first distance from the back. The back may have one or more mounting components, e.g., for mounting on a wall or vertical bars. The row of slots may be angled relative to a vertical orientation of the rack, may have pins to properly align electronic devices during insertion, may have magnets to secure electronic devices, may have power connections, may have electrical contacts/pins on their bottoms or sides, and/or may have contactless charging mechanisms. The slots may have openings in bottom portions, for example, to allow water or trash to fall through without clogging up the inside of the slots or preventing charging.

The charging station has sides adjacent to the row of slots and extending a second distance from the back. The second distance (e.g., of the sides) may greater than the first distance (e.g., of the slots). The relatively shorter first distance that the row of slots extends may be configured so that portions of inserted electronic devices are exposed and thus easily accessible to be grasped or otherwise easily inserted and removed. The relatively greater second distance that the sides extend from the back may be configured so that the exposed portions of the electronic devices are protected, e.g., by extending as far or farther than the electronic devices extend from the back.

In some implementations, the slots and the electronic devices are shaped such that each of the electronic devices fits in a slot in only a single orientation. Each of the electronic devices may have a bump portion such that it fits in a slots in only a single orientation. Such a bump portion of an electronic device may be configured to provide an angled viewing surface when the electronic devices is resting on a horizontal surface.

In some implementations, a charging station includes indicators (e.g., lights) that indicate electronic devices changing charging status of one or more electronic devices and/or that indicate that one or more electronic devices are correctly or incorrectly seated in the slots.

In some implementations, a charging station has a lock for securing a plurality of electronic devices. For example, a charging station may include a locking pin, bar, or roll top cover that prevents removal of one or more electronic devices. In some implementations, electronic devices can be returned to but not released from the charging station when the lock is in a locked state.

Some implementations provide devices, systems, or methods that track a user (e.g., inmate) checking out or checking in an electronic device, e.g., from a charging station. In some implementations, a method is performed by a computing device such as a charging station device or a device communicatively coupled with a charging station device. The method identifies a charging station event at the charging station involving a user removing an electronic device from a receiving portion of the charging station (e.g., checking out a tablet) or the user returning the electronic device to the receiving portion of the charging station (e.g., checking in a tablet). In some implementations, the charging station event is detected based on detecting a power transfer connection being established or discontinued in the receiving portion.

The method further involves identifying the electronic device involved in the charging station event. In one example, the electronic device is identified based on receiving a scanned identifier (bar code) associated with the electronic device, e.g., a bar code on the electronic device itself. In another example, the electronic device is identified based on detecting that the electronic device has changed communication status with the charging station, e.g., connected to disconnected or vice versa, or changed charging status within an event time window, e.g., charging to not charging or vice versa. For example, the method may detect that only one device of ten electronic devices is no longer connected and thus infer that the device that is no longer connected must be the device that was checked out.

The method further involves identifying the user involved in the charging station event. In one example, the user (e.g., inmate) is identified based on an image of the user from a camera on the electronic device or a camera on the charging station at or within an event time window. In another example, the user is identified based on a thumbprint or other biometric reading captured by the electronic device or the charging station. In another example, the user is identified based on the user providing a personal identification number (PIN). In some implementations, a user interface on the charging station or electronic device guides the user through a checkin/checkout process to capture images and/ or other information of the user and the electronic device.

The method also involves tracking use of the electronic device based on identifying the electronic device and the user involved in the charging station event. For example, this may involve determining a period of time that the device was checked out to a user, the applications or content used on the electronic device, the locations within the confinement facility that the electronic device was taken, power usage on the electronic device, data transmission usage on the electronic device, telephone calls made via the electronic device, video conference calls made via the electronic device, and any other usage of the electronic device that is relevant to a tracking system. In one implementation, tracking the use of the electronic device involves determining a period of time that the electronic device was used by the user based on a check-out charging station event and a check-in charging station event. The method may involve detecting a condition of the electronic device based on an image of the electronic device, e.g., comparing before and after images to identify damage.

Some implementations provide devices, systems, or methods that identify damage to an electronic device while it is checked out from a charging station. In some implementations, a method is performed by a computing device such as a charging station device or a device communicatively coupled with a charging station device. The method identifies a check-out charging station event at a charging station, the check-out charging station event involving a user removing an electronic device from a receiving portion of the charging station (e.g., checking out a tablet). The method involves identifying a check-in charging station event at the charging station, the check-in charging station event involving the user returning the electronic device to the receiving portion of the charging station; and (e.g., checking in a tablet). The method in determines a change in condition of the electronic device based on a first condition of the electronic device at the check-out charging station event and a second condition of the electronic device at the check-in charging station event. The change may be determined based on images of the electronic device at the check-out charging station event and the check-in charging station event.

Some implementations identify a check-out charging station event at a charging based on detecting an electronic device being removed from the charging station, identify a check-in charging station event at the charging station based on detecting the electronic device being inserted into a receiving portion of the charging station. Based on identifying the check-in charging station event, a diagnostic is triggered and performed at the electronic device or charging station. The diagnostic may determine a change in condition of the electronic device occurring between the check-out charging station event and the check-in charging station event.

In accordance with some implementations, a non-transitory computer readable storage medium has stored therein instructions that are computer-executable to perform or cause performance of any of the methods described herein. In accordance with some implementations, a device includes one or more processors, a non-transitory memory, and one or more programs; the one or more programs are stored in the non-transitory memory and configured to be executed by the one or more processors and the one or more programs include instructions for performing or causing performance of any of the methods described herein.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

FIG. 7 is side view of the charging station of FIG. 6 with electronic devices inserted.

FIG. 9 is an exploded view of components of a charging station.

FIG. 10 is an exploded view of folding components of a charging station.

FIG. 11 is an exploded view of folding components of a charging station.

FIGS. 15A and 15B are block diagrams illustrating locking pin-based locking mechanism of a charging station.

FIG. 16 is a rear view of an exemplary electronic device capable of being charged via a charging station.

FIG. 17 is a side view of the electronic device of FIG. 16.

FIG. 18 is a side view of the electronic device of FIG. 16.

FIG. 19 is a front view of the electronic device of FIG. 16.

Figure 1:
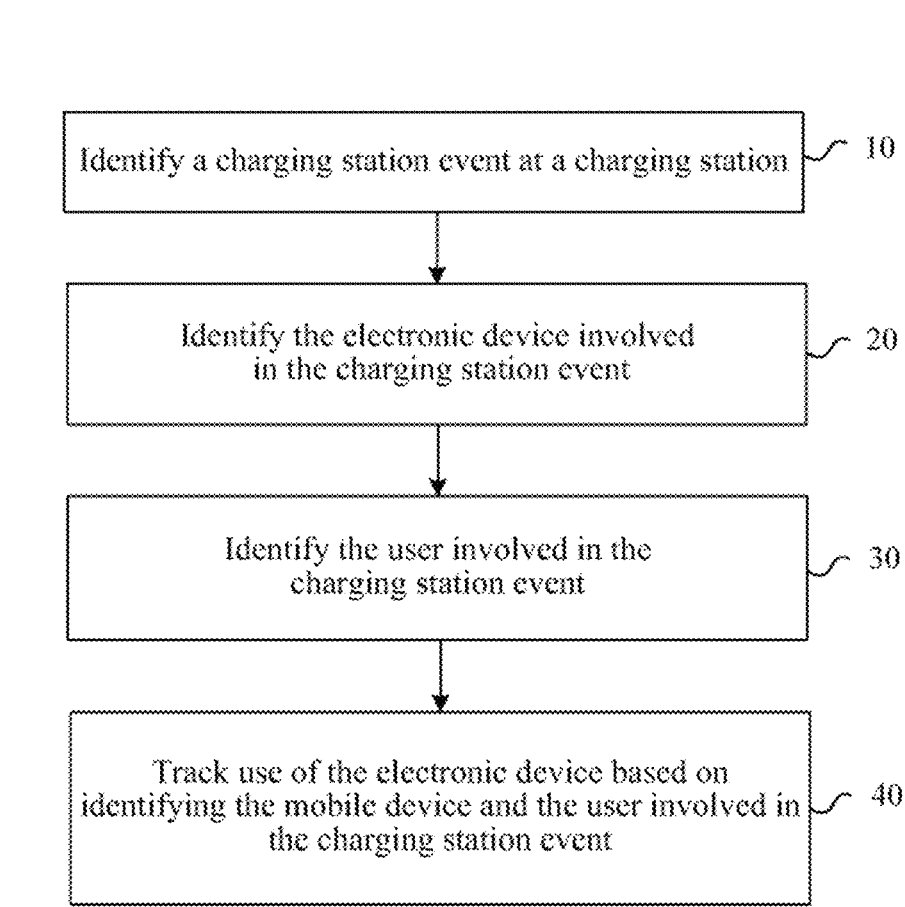
FIG. 1 is a flow chart illustrating an exemplary method of tracking use of an electronic device.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects or variants do not include all of the specific details described herein. Moreover, well-systems, methods, components, devices and circuits have not been described in exhaustive detail so as not to obscure more pertinent aspects of the example implementations described herein.

FIG. 1 is a flow chart illustrating an exemplary method 5 of tracking use of an electronic device. In some implementations, the method 5 is performed by a device (e.g., charging station 100 or management unit 200 of FIGS. 3-5). The method 5 can be performed by a single device or multiple devices in communication with one another. In some implementations, the method 5 is performed by processing logic, including hardware, firmware, software, or a combination thereof. In some implementations, the method 5 is performed by a processor executing code stored in a non-transitory computer-readable medium (e.g., a memory).

At block 10, the method 5 identifies a charging station event at the charging station. The charging station has one or more receiving portions (e.g., charging slots) for charging one or more electronic devices simultaneously. The charging station event may involve a user removing an electronic device from a receiving portion of the charging station (e.g., checking out a tablet) or the user returning the electronic device to the receiving portion of the charging station (e.g., checking in a tablet). In some implementations, the charging station event is detected based on detecting a power transfer connection being established or discontinued in the receiving portion.

At block 20, the method 5 identifies the electronic device involved in the charging station event. The electronic device may be identified based on user input or an image, scan, or sound captured at the charging station. The electronic device may be identified based on an image of an identifier (e.g., a bar code) associated with the electronic device, e.g., a bar code on the electronic device itself. The electronic device may be identified based on a computer vision object detection of an image of the electronic device.

In another example, the electronic device is identified based on detecting that the electronic device has changed communication status with the charging station or changed charging status within an event time window-connected versus disconnected or charging versus not charging. For example, the method 5 may detect that only one device of ten or twelve devices has been disconnected within an event time window (e.g., within the last 30 seconds) and thus infer that the device that is no longer connected must be the device that was checked out. Similarly, the method 5 may detect that only one device of the ten or twelve devices has been connected within an event time window and thus infer that the device that was recently connected must be the device that was checked in. In some implementations, identifying an electronic device involves monitoring the charging status of a plurality of electronic devices and identifying that the electronic device is the only electronic device of the multiple electronic devices to change charging status within a charging event time window. If multiple electronic devices change charging status within the window, the method 5 may request additional input or user action (e.g., e.g., requesting that one of two devices that were disconnected be reconnected). In another example, only a single device is unlocked for a user to remove and the electronic device is identified based on that unlocking.

In some implementations, the electronic device is identified based on a communication received from the electronic device that identifies the device. For example, an electronic device may be configured to detect when its charging status changes and automatically send a message to the charging station or remote controller to provide notification of the change. In other examples, the electronic device sends a communication identifying the electronic device in response to another triggering events, e.g., the user providing input on the device, the device being detected within a particular area or threshold distance from the charging station or another reference point or device within the confinement institution, etc.

At block 30, the method 5 identifies which user was involved in the charging station event. In one example, the user (e.g., inmate) is identified based on an image of the user from a camera on the electronic device or a camera on the charging station at or within an event time window. In some implementations, the system stores a reference image or model of each of the multiple users who may access the electronic devices, captures one or more images of the environment around the charging station and/or electronic device during a charging station event time window, and performs a computer vision analysis, machine learning analysis, or computer-based algorithm to identify one or more individuals involved in the charging station event. In some implementations, multiple individuals are within the environment around the charging station during the charging station event time window and a computer vision technique, machine learning technique, or computer-based algorithm is used to select one of the multiple users as the user involved in the event. In some implementations, the user is identified based on performing computer vision-based face detection on an image of the user.

In some implementations, the user is identified based on creating a three dimensional model of the user using data obtained from an infrared projector and camera, an RGB-D camera, or another 3D model creation technique. A 3D model of one or more individuals near the charging station during a charging station event window may be compared with 3D models of individuals stored in a reference data set to identify those individuals.

In some implementations, multiple individuals are identified and the system provides instructions or receives input to identify which individual is involved in the charging station event, e.g., providing visual or audio content asking individuals not involved in the event to move away from the charging station in order to complete the event or asking the user for input to clarify which individual is involved in the event.

In some implementations, the user is identified based on a thumbprint or other biometric reading captured by the electronic device or the charging station. For example, the charging station and/or electronic device may prompt the user to provide a thumb print or hold the device up in front of the user's face so that an image of the user's face, eye, or other distinguishing physical characteristics can be captured and used for biometric-based identification.

In some implementations a user is identified by a voice sample that is recorded during a charging station event time window. Sounds in the environment may be separated based on a sound analysis to distinguish sounds near the charging station or electronic device from sounds farther away to distinguish the user involved in the charging station event from users and other sound sources not involved in the event. In some implementations, the user is asked to provide a voice sample during the charging station event, e.g., asked to say a particular word or phrase, to facilitate or improve the accuracy of sound-based user identification.

In some implementations, the user is identified based on the user providing a personal identification number (PIN), password, login credentials, or other user input at the charging station or on the electronic device.

In some implementations, for check-in type events the user is identified based on the electronic device. For example, the user may be determined to be the same user that currently has the electronic device checked out or that most recently checked out the electronic device.

In some implementations, a user interface on the charging station or electronic device provides visual or audible instructions to guide the user through a checkin/checkout process. The process may involve the user providing certain information or performing certain actions. The process may involve instructing the user so that appropriate images and/or other information of the user and/or the electronic device are received.

At block 40, the method 5 tracks use of the electronic device based on identifying the electronic device and the user involved in the charging station event. For example, this may involve determining a period of time that the device was checked out to a user, the applications or content used on the electronic device, the locations within the confinement facility that the electronic device was taken, power usage on the electronic device, data transmission usage on the electronic device, telephone calls made via the electronic device, video conference calls made via the electronic device, and any other usage of the electronic device that is relevant to a tracking system. In one implementation, tracking the use of the electronic device involves determining a period of time that the electronic device was used by the user based on a check-out charging station event and a check-in charging station event. The method may involve detecting a condition of the electronic device based on an image of the electronic device, e.g., comparing before and after images to identify damage.

Figure 2:
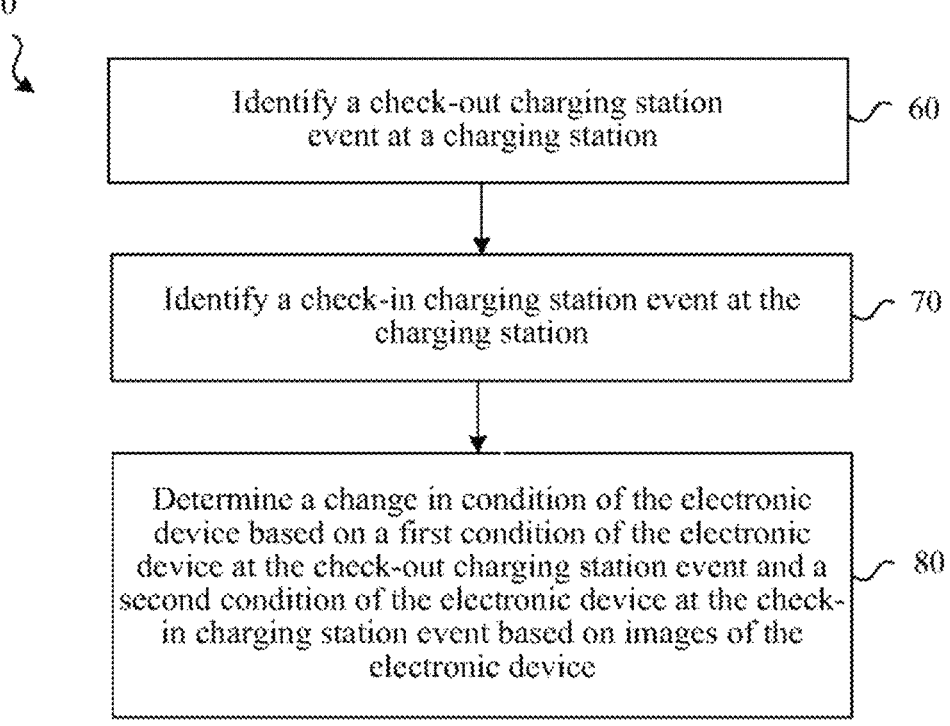
FIG. 2 is a flow chart illustrating an exemplary method of determining a change in condition of an electronic device.

FIG. 2 is a flow chart illustrating an exemplary method 50 of determining a change in condition of an electronic device. In some implementations, the method 50 is performed by a device (e.g., charging station 100 or management unit 200 of FIGS. 3-5). The method 50 can be performed by a single device or multiple devices in communication with one another. In some implementations, the method 50 is performed by processing logic, including hardware, firmware, software, or a combination thereof. In some implementations, the method 50 is performed by a processor executing code stored in a non-transitory computer-readable medium (e.g., a memory).

At block 60, the method 50 identifies a check-out charging station event at a charging station. The check-out charging station event may involve a user removing an electronic device from a receiving portion of the charging station (e.g., checking out a tablet). Identifying the event may involve identifying the user involved, the electronic device involved, and capturing information and images of the user, electronic device, and circumstances during an event window.

Based on identifying the check-out charging station event, input identifying a current condition of the electronic device may be required before enabling access to functionality on the electronic device. In some implementations, based on identifying the check-out charging station event, access to functionality on the electronic device is disabled and input confirming that the electronic device is undamaged and operational requested. Based on receiving input confirming that the electronic device is undamaged and operational, functionality on the electronic device is enabled. The provision of functionality on the electronic device may be provided contingent upon receiving input that accepts responsibility for any changes of condition to the electronic device that may occur during use of the electronic device.

Some implementations, receive input from the user at a time of the check-out charging station event that identifies a defect or issue present at the time of the check-out charging station event. The existence of the defect or issue may be confirmed or established (e.g., via capturing images or sensor data or running a diagnostic) prior to enabling access to functionality on the electronic device.

At block 70, the method 50 identifies a check-in charging station event at the charging station. The check-in charging station event may involve the user returning the electronic device to the receiving portion of the charging station. Identifying the check-in charging station event may involve identifying that a particular electronic device has been reconnected or reinserted into a slot of a charging station. Identifying the electronic device may be based by an electronic communication between the electronic device and the charging station, an image of the electronic device during an event window, and/or information provided by the user.

Based on identifying the check-in charging station event, a diagnostic may be triggered and performed at the electronic device or charging station. The diagnostic may determine a change in condition of the electronic device occurring between the check-out charging station event and the check-in charging station event. Additional checkout of the electronic device may be prohibited and/or disabled while the diagnostic is performed. In some implementations, a change in condition of an electronic device is attributed to a particular user, e.g., a user involved in the check-out charging station event.

In some implementations, a diagnostic detects a change in condition that is a cracking or shattering of a display surface of the electronic device. For example, a sound, acoustic, and/or vibration sensor may detect sound and/or vibration that is interpreted to identify a glass shattering event or condition. In another example, display elements provide feedback indicative of a cracking or shattering. An image of the electronic device may be evaluated, e.g., via a computer vision algorithm, machine learning, model, etc. to identify cracking or shattering of the electronic device.

In some implementations, a diagnostic detects a change in condition that is a change in device capability for wireless network connection, e.g., Wi-Fi no longer working due to transmission component damage or tampering with physical components of the device, as examples. The diagnostic may attempt an electronic communication with the device when the device is in a condition in which communication is expected (e.g., when the device has power and/or is turned on and/or in range of a Wi-Fi signal.

In some implementations, a diagnostic detects a change in condition that is a change in operational capability (e.g., will the device turn on, load the operating system, receive input from its touch screen, etc.). Some implementations, provide power to the electronic device while the electronic device is inserted into the charging station and, based on power being provided to the electronic device, determine that the change in condition is attributable to a cause other than a dead battery, e.g., due to damage to the device.

In some implementations, a diagnostic assesses motion sensor data of one or more motion sensors of the electronic device to attribute the change in condition with an activity occurring between the check-out charging station event and the check-in charging station event. For example, based on the sensor data, the diagnostic attributes the change in condition with the electronic device having been dropped between the check-out charging station event and the check-in charging station event. In another example, based on the sensor data, the diagnostic attributes the change in condition with an impact between the electronic device and another object or structure. Drops, throws, impacts, and other undesirable activities may be detected based on motion sensor data including, but not limited to, using information from gyroscopes, accelerometers, and/or image sensors. G-Forces and other motion attributes may be detected and used to determine particular activities as having occurred.

The diagnostic may classify the change in condition using a neural network as one of a set of conditions, e.g., as having a cracked/shattered display, transmission component damage, as no longer turning on, as no longer booting the operating system, etc.

In some implementations, based on detecting a change in condition, an explanation of the change in condition is requested from the user who had the device during a period at which the change was determined to have occurred. The request may be requested when the user next attempts to check-out the same or another device. The user may be prohibited from accessing functionality on the same or different devices until the user responds to request and/or pays to fix damage or otherwise address the change in condition. Input may be received from the user. The input may provide an explanation for a defect or issue with the electronic device identified at the check-in charging station event and/or provide payment or consent to use of funds to pay to fix damage or otherwise address the change in condition.

At block 80, the method 50 determines a change in condition of the electronic device based on a first condition of the electronic device at the check-out charging station event and a second condition of the electronic device at the check-in charging station event. The change may be determined based on images of the electronic device at the check-out charging station event and the check-in charging station event. For example, a computer vision technique may be used to score or evaluate the first condition of the electronic device at the check-out charging station event and a second condition of the electronic device at the check-in charging station event. In some implementations, a user is instructed to hold, position, or move the electronic device in view of a camera so that images or video of the electronic device from multiple perspectives are captured. In some implementations, scratches, dents, cracks, or other physical damage to exterior surfaces of the electronic device are identified. In some implementations, a machine learning process is used to evaluate the conditions or change in condition of the electronic device, e.g., using a neural network trained using images of electronic devices in various conditions (e.g., good, cracked, dented, etc.) In some implementations, the conditions of the electronic device are determined based on diagnostic software executed on the electronic device or charging station at the time of the check-out and check in charging station events.

In some implementations, the user is guided through an evaluation process in which the user provides explanations or comments about the electronic device. For example, the user may be asked to identify any defects or other issues with the electronic device at checkout. The user need not be responsible for defects and other issues that were present prior to the inmate's checking out the device and may be given the opportunity to identify such issues that are not otherwise automatically detected. As another example, the user may be asked to provide an explanation for any defects or other issues with the electronic device that are identified at check-in.

In the case of a change in condition of an electronic device, a repair process may be initiated, e.g., by contacting a service technician or repair service of the identity of the electronic device, the change in condition, and/or payment information to pay for the repair provided by an inmate responsible for the change in condition.

Exemplary Multi-Device Charging/Monitoring System

Figure 3:
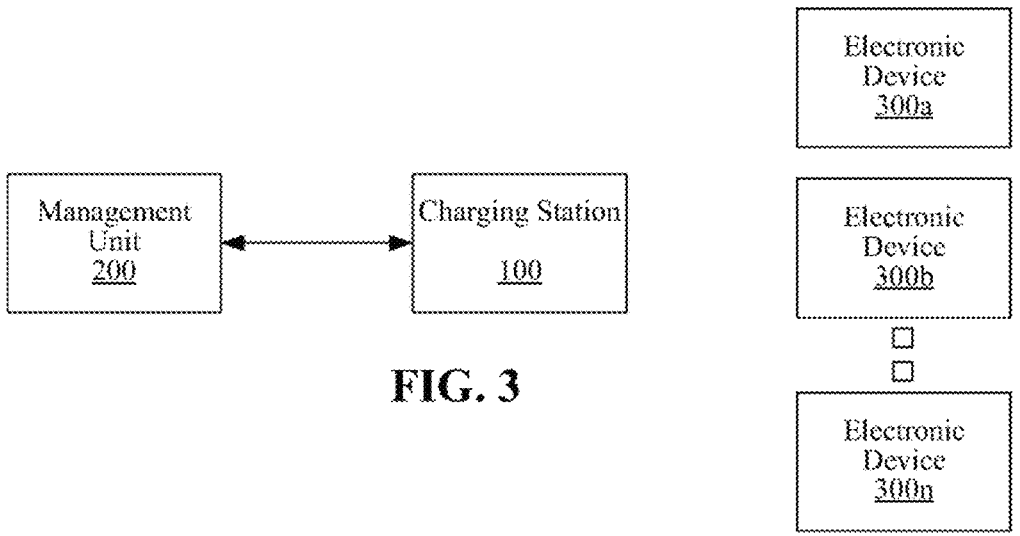
FIG. 3 is a block diagram of an example environment for certain implementations disclosed herein.
Figure 4:
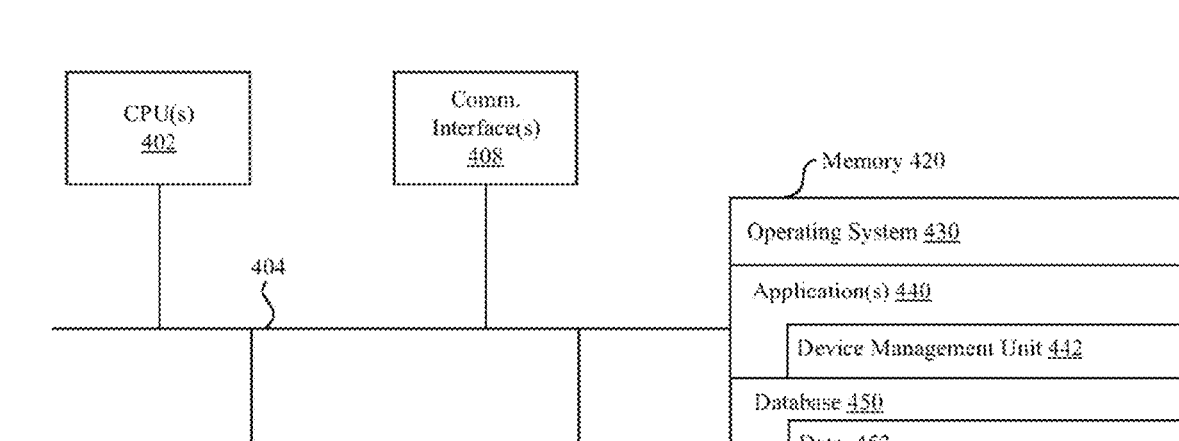
FIG. 4 is a block diagram of computing components of an example charging station.
Figure 5:
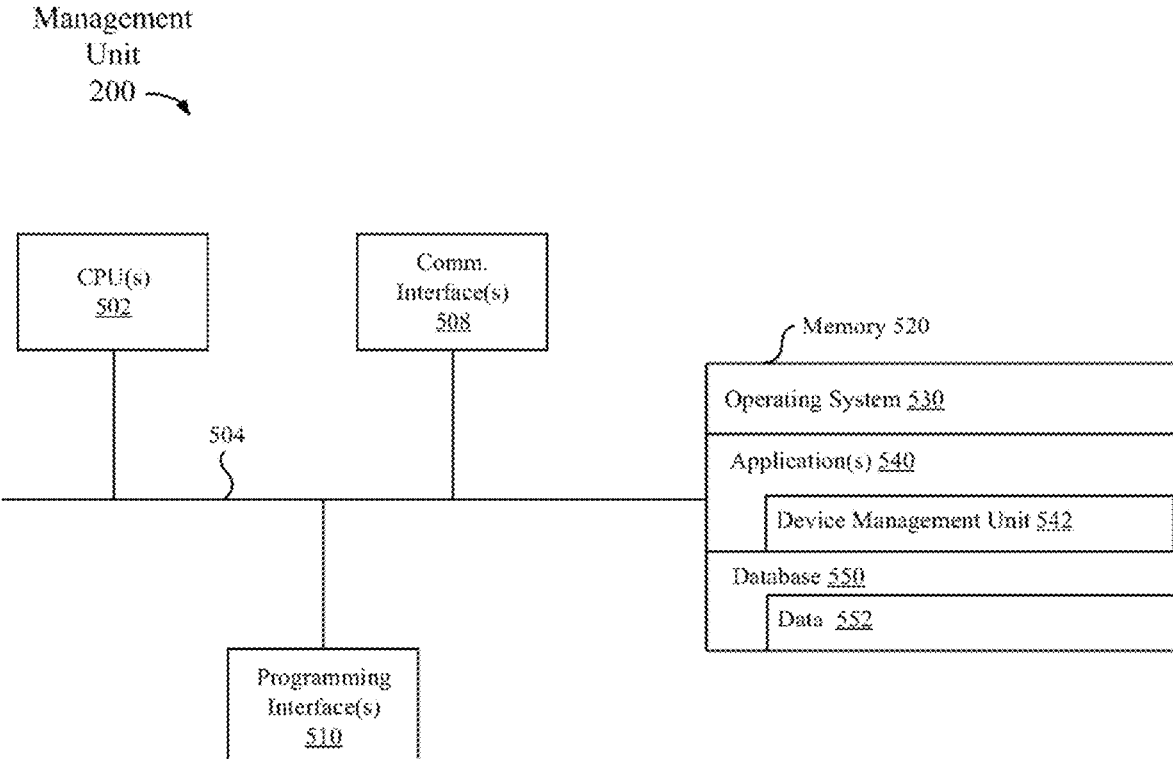
FIG. 5 is a block diagram of computing components of an example management unit.

FIGS. 3-5 illustrate an example environment for certain implementations disclosed herein. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the environment includes a charging station 100 and management unit 200, one or both of which may be in a confinement institution.

In some implementations, the management unit 200 is configured to manage and coordinate the charging and use of electronic devices 300a-n at the charging station 100 within the confinement institution. In some implementations, the management unit 200 includes a suitable combination of software, firmware, or hardware. The management unit 200 is described in greater detail below with respect to FIG. 3.

In some implementations, the management unit 200 is a computing device that is local or remote relative to the confinement institution. In one example, the management unit 200 is a desktop computer used by confinement institution personnel. In one example, the management unit 200 is a local server located within the confinement institution. In another example, the management unit 200 is a remote server located outside of the confinement institution (e.g., a cloud server, central server, etc.). In some implementations, the management unit 200 is communicatively coupled with the charging station 100 via one or more wired or wireless communication channels (e.g., BLUETOOTH, IEEE 802.11x, IEEE 802.16x, IEEE 802.3x, etc.).

In some implementations, the charging station 100 is configured to charge multiple electronic devices 300a-n simultaneously. In some implementations, the charging station 100 includes a suitable combination of software, firmware, or hardware for itself managing the charging and use of the electronic devices 300a-n. The charging station 100 is described in greater detail below with respect to FIG. 2. In some implementations, the functionalities of the management unit 200 are provided by or combined with the charging station 100, for example, in the case of charging station that functions as a stand-alone unit.

The electronic devices 300a-n may include processing units (e.g., microprocessors, ASICs, FPGAs, GPUs, CPUs, processing cores, or the like), input/output (I/O) devices and sensors, communication interfaces (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, 12C, or the like type interface), programming (e.g., I/O) interfaces, displays, image sensor systems, memory, and communication buses 504 for interconnecting these and various other components. The I/O devices and sensors may include an inertial measurement unit (IMU), an accelerometer, a magnetometer, a gyroscope, a thermometer, one or more physiological sensors (e.g., blood pressure monitor, heart rate monitor, blood oxygen sensor, blood glucose sensor, etc.), one or more microphones, one or more speakers, a haptics engine, one or more depth sensors (e.g., a structured light, a time-of-flight, or the like), or the like. Information from the I/O devices and sensors may be communicated to the charging station 100 and/or management unit 200 to facilitate the charging and management of the electronic devices 300a-n.

FIG. 4 is a block diagram of an example of the charging station 100 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the charging station 100 includes one or more processing units 402 (e.g., microprocessors, application-specific integrated-circuits (ASICs), field-programmable gate arrays (FPGAs), graphics processing units (GPUs), central processing units (CPUs), processing cores, or the like), one or more input/output (I/O) devices 406, one or more communication interfaces 408 (e.g., universal serial bus (USB), FIREWIRE, THUNDERBOLT, IEEE 802.3x, IEEE 802.11x, IEEE 802.16x, global system for mobile communications (GSM), code division multiple access (CDMA), time division multiple access (TDMA), global positioning system (GPS), infrared (IR), BLUETOOTH, ZIGBEE, or the like type interface), one or more programming (e.g., I/O) interfaces 410, a memory 420, and one or more communication buses 404 for interconnecting these and various other components.

In some implementations, the one or more communication buses 404 include circuitry that interconnects and controls communications between system components. In some implementations, the one or more I/O devices 406 include at least one of a keyboard, a mouse, a touchpad, a joystick, one or more microphones, one or more speakers, a thermometer, physiological sensors (e.g., blood pressure monitor, heart rate monitor, blood oxygen sensor, blood glucose sensor, etc.), one or more biometric sensors, one or more microphones, one or more speakers, one or more depth sensors (e.g., a structured light, a time-of-flight, or the like), one or more displays or touch screens, or the like.

The memory 420 includes high-speed random-access memory, such as dynamic random-access memory (DRAM), static random-access memory (SRAM), double-data-rate random-access memory (DDR RAM), or other random-access solid-state memory devices. In some implementations, the memory 420 includes non-volatile memory, such as one or more magnetic disk storage devices, optical disk storage devices, flash memory devices, or other non-volatile solid-state storage devices. The memory 420 optionally includes one or more storage devices remotely located from the one or more processing units 402. The memory 420 comprises a non-transitory computer readable storage medium. In some implementations, the memory 420 or the non-transitory computer readable storage medium of the memory 420 stores the following programs, modules and data structures, or a subset thereof including an optional operating system 430, applications 440, and database 450. The applications 440 can include on more applications, such as application 442, configured to facilitate charging and use of the electronic devices. The database 450 can include data 452 about the electronic devices, inmate users, non-inmate users (e.g., officers, police, counselors, lawyers, prisoner friends and family, etc.), the confinement institution layout, the confinement institution systems (e.g., electrical, communication, etc.), and any other information useful by the applications 440.

Although these modules and units are shown as residing on a single device (e.g., the charging station 100), it should be understood that in other implementations, any combination of these modules and units may be located in separate computing devices. Moreover, FIG. 4 is intended more as functional description of the various features which are present in a particular implementation as opposed to a structural schematic of the implementations described herein. As recognized by those of ordinary skill in the art, items shown separately could be combined and some items could be separated. For example, some functional modules shown separately in FIG. 4 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, or firmware chosen for a particular implementation.

FIG. 5 is a block diagram of an example of the management unit 200 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the management unit 200 includes one or more processing units 502 (e.g., microprocessors, ASICs, FPGAs, GPUs, CPUs, processing cores, or the like), one or more communication interfaces 508 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, I2C, or the like type interface), one or more programming (e.g., I/O) interfaces 510, a memory 520, and one or more communication buses 504 for interconnecting these and various other components.

In some implementations, the one or more communication buses 504 include circuitry that interconnects and controls communications between system components. The memory 520 includes high-speed random-access memory, such as DRAM, SRAM, DDR RAM, or other random-access solid-state memory devices. In some implementations, the memory 520 includes non-volatile memory, such as one or more magnetic disk storage devices, optical disk storage devices, flash memory devices, or other non-volatile solid-state storage devices. The memory 520 optionally includes one or more storage devices remotely located from the one or more processing units 502. The memory 520 comprises a non-transitory computer readable storage medium. In some implementations, the memory 520 or the non-transitory computer readable storage medium of the memory 520 stores the following programs, modules and data structures, or a subset thereof including an optional operating system 530, applications 540, and database 550. The applications 540 can include on more applications, such as application 542, configured to facilitate charging and use of the electronic devices. The database 550 can include data 552 about the electronic devices, inmate users, non-inmate users (e.g., officers, police, counselors, lawyers, prisoner friends and family, etc.), the confinement institution layout, the confinement institution systems (e.g., electrical, communication, etc.), and any other information useful by the applications 440.

Moreover, FIG. 5 is intended more as a functional description of the various features which are present in a particular implementation as opposed to a structural schematic of the implementations described herein. As recognized by those of ordinary skill in the art, items shown separately could be combined and some items could be separated. For example, some functional modules shown separately in FIG. 5 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, or firmware chosen for a particular implementation.

Exemplary Multi-Device Charging Station

Figure 6:
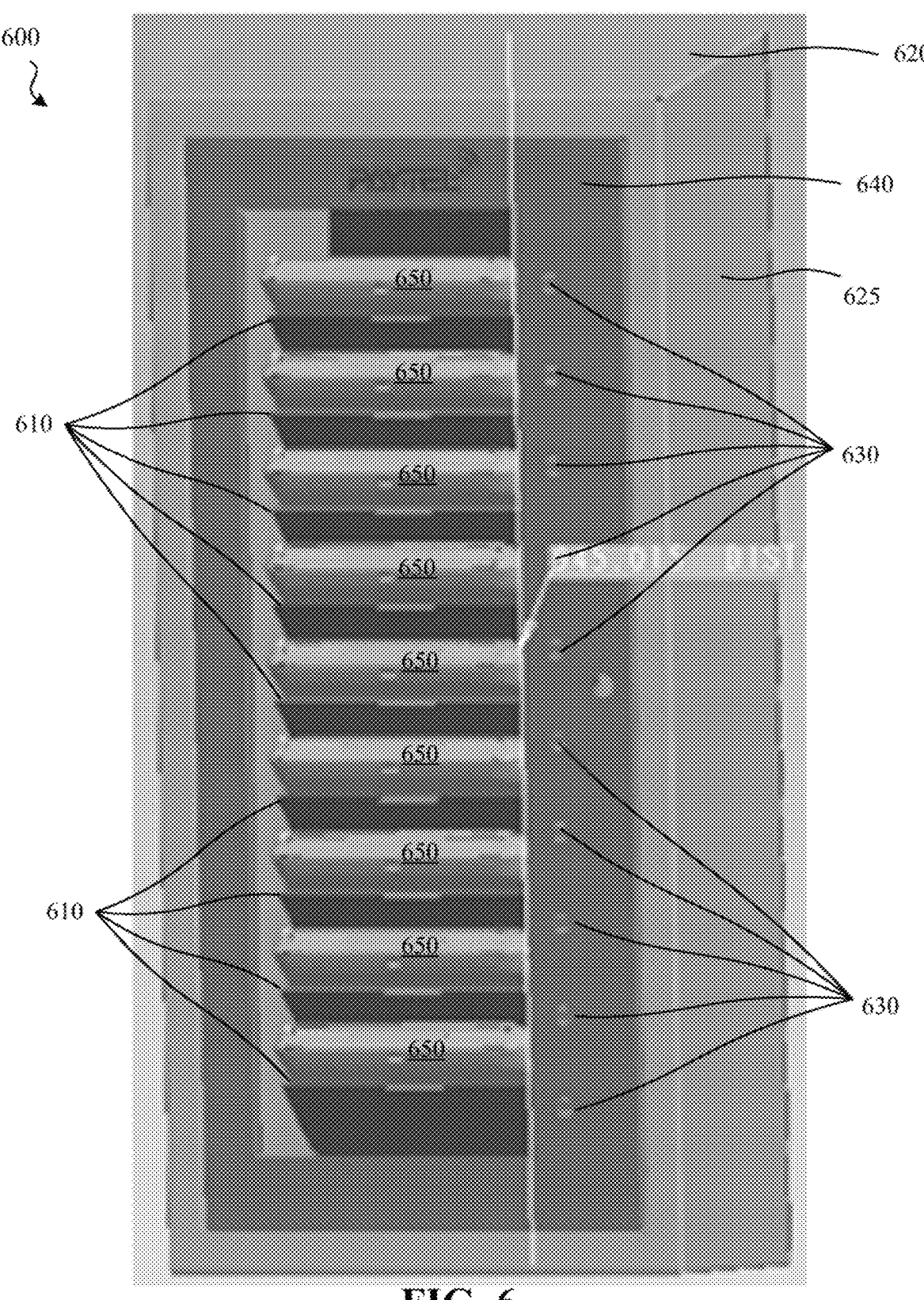
FIG. 6 is a perspective view of an example charging station.
Figure 8:
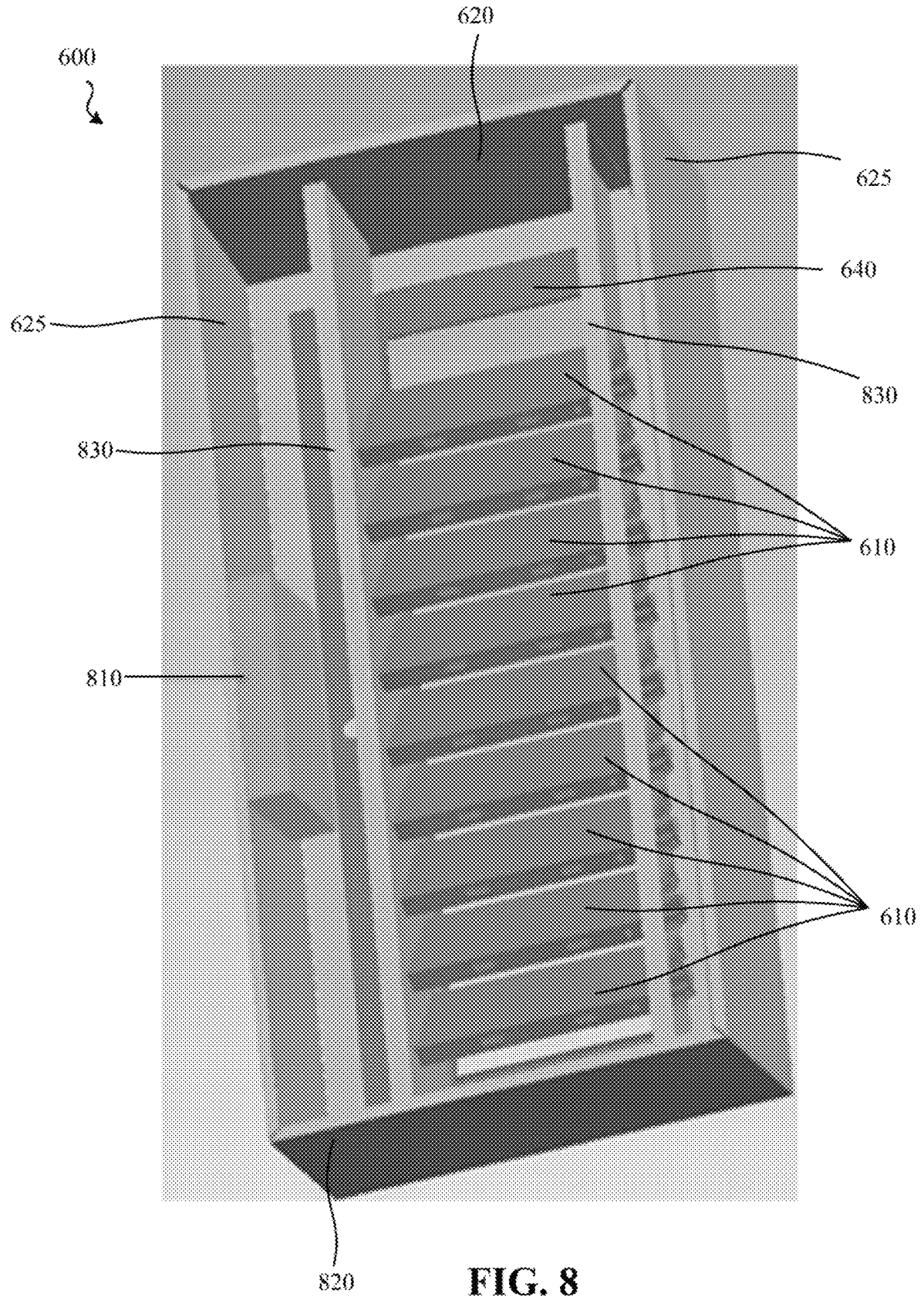
FIG. 8 is a perspective view of the charging station of FIG. 6.
Figure 12:
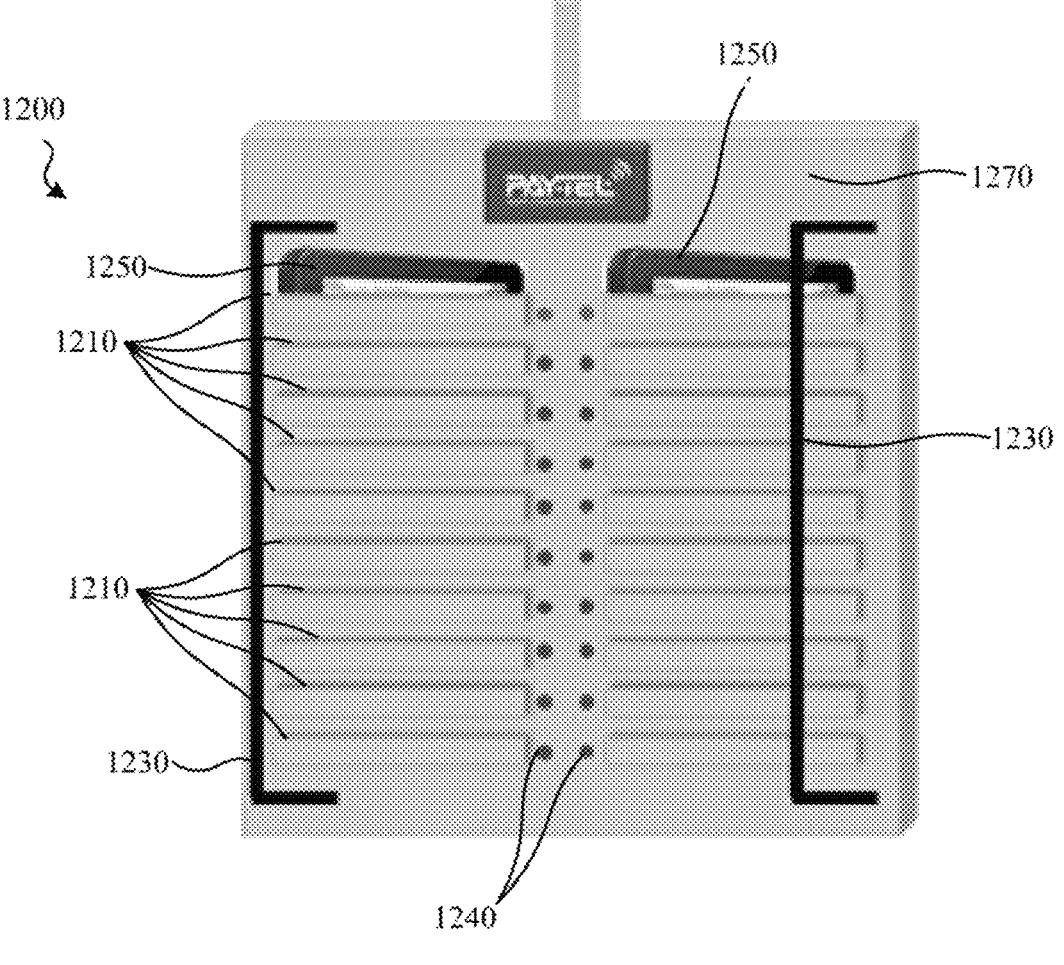
FIG. 12 is a front view of another example charging station.

FIGS. 6-8 illustrate an example charging station 600. The charging station 600 includes multiple slots 610 into which electronic devices 650 have been inserted for charging. The slots 610 are in a rack such that the slots 610 are angled relative to a vertical orientation of the rack. The slots may be supported by supports 830 (FIG. 8). The slots 610 may have pins to properly align electronic devices 650 during insertion. The slots 610 may have magnets to secure electronic devices 650. The slots 610 may have power connections, e.g., electrical contacts/pins on their bottoms or sides and/or contactless charging mechanisms. The use of non-plug-based and wireless electrical power mechanisms can provide significant advantages. Avoiding or limiting the use of plugs and wires is particular useful in the context of confinement institutions in which wires can be safety hazards and plugs may detract from device durability.

The slots 610 may have openings in bottom portions, for example, to allow water or trash to fall through without clogging up the inside of the slots or preventing charging.

The charging stations 600 is configured to attach to or be positioned adjacent to a wall in a confinement institution and to simultaneously charge multiple tablets, mobile phones, laptops, or other portable electronic devices 650. The charging station 600 is configured with a slim profile, for example, in some implementations extending from the wall less than 6 inches, less than 12 inches, less than 18 inches, or less than 24 inches. Such a slim profile may be less likely to interfere with doors, corridor traffic, and room usage and may make the charging station 600 less likely to be damaged. In some implementations, the charging station 600 is configured to use significantly less space that a cart-based or box charger and is suitable for installation in narrow hallways and rooms with various space constraints.

The charging station 600 is configured with protective features that may help protect inserted electronic devices 650 (e.g., tablets) from damage. The charging station 600 includes a casing including a top surface 620, side surface 625, and bottom surface 820 configured to enclose internal components 810, e.g., processors, memory, etc., and to protect electronic devices 650 that are inserted for charging. For example, the row of slots 610 with electronic devices 650 may extend a first distance 720 from the back and the charging station 600 may have sides, e.g., side surfaces 625, adjacent to the row of slots 610 and extending a second, greater distance 710 from the back. The slots 610 may be configured so that portions of inserted electronic devices 650 are exposed and thus easily accessible to be grasped or otherwise easily inserted and removed. The relatively greater second distance 710 may be configured so that the exposed portions of the electronic devices 650 are protected, e.g., by extending as far or farther than the electronic devices 650 extend from the back.

Indicators 630 are color lights that, in this example, indicate a charging status of each of the inserted electronic devices 650 (e.g., red indicates charging, green indicates fully charged, etc.) and/or that indicate that electronic devices 650 are correctly or incorrectly seated in the slots 610.

Front panel 640 on the front of the charging station 600 is configured to open to allow user access to the electronic devices 650. In this example, the front panel 640 includes a see-through portion or opening through which inserted electronic device 650 may be viewed while the front panel 640 is in a closed position.

In some implementations, the slots 610 and the electronic devices 650 are shaped such that the each of the electronic devices 650 fit in a slot in only a single orientation. Each of the electronic devices 650 may have a bump portion (see FIGS. 16-19) such that each electronic device 650 fits in a each of the slots 610 in only a single orientation.

Such a bump portion of an electronic device 650 may be configured to provide an angled viewing surface when the electronic device 650 is resting on a horizontal surface.

In some implementations, each electronic device 650 has an angled face on at least one side and thus side edges of unequal size, e.g., the bottom edge may be smaller than the right edge, left edge, and top edge. The only the smallest edge may fit into one of the slots 610 of the charging station 600, thus prohibiting an electronic device 650 from being inserted with any of the other three edges leading. In some implementations, the charging station 600 is configured to receive electronic devices 650 inserted only in a portrait orientation. In some implements, the charging station 600 is configured to receive electronic devices 650 inserted only in a landscape orientation.

In some implementations, a charging station 600 has a lock for securing a plurality of electronic devices 650. For example, the charging station 600 may include a locking pin, bar, or roll top cover that prevents removal of one or more electronic devices 650. In some implementations, electronic devices 650 can be returned to but not released from the charging station 600 when the lock is in a locked state.

In some implementations, the charging station 600 is configured for self-service by the individual inmates, controlling the electronic devices 650 such that an inmate is only able to remove an electronic device 650 after checking the electronic device out and tracking when the inmate returns the electronic device 650. The charging station 600 thus enables the controlled distribution and collection of electronic devices 650 without requiring significant officer supervision and time and ultimately conserving the confinement institutions resources.

Various components can be used to secure each electronic device 650 in a charging position and orientation. FIGS. 6-8 illustrates slots 650 into which electronic devices 650 can be received and securely held in a particular orientation (i.e., angled upwardly, or at any other angle). In this example, because of the orientation of the slots 610 and corresponding electronic devices 650, gravity helps secure each electronic device 650 in a respective slot 610 in electrical communication with a charging contact at the bottom of the slot 610. Each electronic device 650 can also have holes (e.g., two holes) that are designed to match up with pins. The holes and the pins seat together to align the electronic device 650 in the proper position.

Magnets can additionally or alternatively be used. In some implementations, the charging station 610 uses magnets to attract each electronic device 650 to the pins or charging contacts and hold each device firmly against such pins/contacts or otherwise securely within the charger. For example, upward facing magnets or metal contacts in the bottom of each slot 610 into which each electronic device 650 is received can magnetically interact with corresponding magnets or metal contacts on each electronic device 650.

The angled orientation of the slots 610 and corresponding electronic devices 650 (when inserted) reduces the required thickness of the charging station 600, e.g., enabling the charging station 600 to a have a slimmer (e.g., closer to the wall) profile than otherwise. In some implementations, the charging station 600 is configured to fold or otherwise transform to further reduce its profile or protect the electronic devices 650.

The charging station 600 can have various features that facilitate mounting to a wall including, but not limited to, fasteners, mounting brackets, screw holes, magnets, etc. In some implementations, a wall-mounted charging station rests on an underlying floor surface to provide all or some of its support. In other implementations, the charging station 600 does not rest on the floor and the mounting features provide sufficient support to retain the charging station 600 in a fixed position relative to the wall without floor support. In some implementations a wall-mounted charging station 600 is supported partially or entirely from a support that extends from a ceiling, overhanging beam, or other support. In some implementations, the charging station 600 can be raised and lowered, for example, to raise the charger and associated electronic devices 60 to minimize interference with facility space or restrict inmate access to the devices when not in use or during device-restricted time periods.

In some implementations, a charging station 600 is installed on cell bars, a mobile cart, or a vehicle.

In some implementations, one or more charging stations 600 are connected using a mounting bracket that allows technicians to service the unit(s) while still hanging on the wall/and or using a face frame that is easily removable (or hinged). In some implementations, the charging station 600 is mounted on a roll around cart, or standing cart, bars, or with an optional stand so it will sit on a table/floor or other flat surface.

In some implementations, a wall-mounted charging station is mounted to a confinement facility wall using a hanging plate. FIGS. 9-11 illustrate components for hanging a charging station. In this example, a hanging plate 1310 is configured with openings for screws, bolts, or other fasteners to be secured to a wall. The hanging plate 1310 will hold the charging station once installed. The back plate 1310 is configured with an opening that enables it to be installed over the hanging plate 1310. The back plate 1310 may also be fastened to the wall using screws, bolts, or other fasteners. The charging rack 1330 includes slots for charging electronic devices and is configured to be inserted into and supported by the back plate 1320. The charging rack 1330 may include wiring that is hidden behind the front cover 1340. The front cover 1340 attaches (e.g., via screws) to the back plate 1320 to provide protection and a finished appearance.

In some implementations, as illustrated in FIGS. 10 and 11, the front cover 1340 is attached via a hinge 1430 to make it easy for the charging station to be serviced. In one example, the charging station includes a mounting bracket installed on the wall. In this example, the front panel is able to swing away from the wall on the hinge 1430. This may enable a service technician to service the charging station without removing it from the wall upon which it is mounted. In some implementations, the hinges 1410 can be removed for service, for example, to enable removing some or all of the charger from the wall. The charging station can include another mechanism that functions in conjunction with the hinges 1430 to limit the movement of the charging station on the hinges 1430. For example, the charging station includes cables 1410 configured to only allow the hinges 1430 to open far enough for service or to create a safe level platform for service. In other implementations, one or more of these functions is achieved with a service hanger that allows all items to hang on the wall without a hinge.

Cameras, microphones, and/or other features of the electronic devices may be used while the electronic devices are charging. In some implementations, the charging station is configured to ensure that each electronic device has a particular orientation as described above. In one such implementation, an electronic device only fits in the charger in one way, with the electronic device's camera facing out into the room away from the charging station. The electronic device is communicatively coupled (e.g., via WIFI) with another device, e.g., charging station 100 or management unit 200, that receives images from the camera on the electronic device at the charging station. In one example, a facility manager uses a management unit 200 to communicate with an electronic device in the charging station 100 to turn the electronic device's camera "on" to investigate what is happening near the electronic device. Microphones on the electronic device can also be remotely enabled to listen to the area. In some implementations, a microphone is enabled while the camera is being used in the charging station. Motion detection alerts could be sent to email, SMS, or any other appropriate device or person.

In some implementations, the charging station 100 or management unit 200 is configured to control an associated electronic device when an electronic device is being inserted into or removed from the charging station. A camera or other sensor on the electronic device is activated or otherwise used to capture an image or other information during the time when the electronic device is inserted into or removed from the charger. In one implementation, a camera captures an image of an inmate (or other person) inserting or removing an electronic device and facial recognition or person identification is used to identify the inmate/person who is automatically associated with the action. Accordingly, a system in this example is configured to track check-in/check-out activities based on automatically detecting actions (e.g., device insertion and device removal) and automatically identifying the person associated with the action. Such as system can retain the images or other inmate/person identifying data for various purposes, for example, to rebut an assertion by an inmate that the inmate did not check-out/remove a given electronic device. In some implementations, the charging station is configured to unlock and allow removal of an electronic device after an image or other information is detected and used to identify which inmate is removing the device. Similarly, inserting a device can be controlled to only allow insertion after inmate identification is complete. Note that inmates can be identified based on RGB image data, RGB-D image data, infrared sensor, sound detection, retina detection, etc. along with a suitable algorithm and data for identifying an inmate. Inmate detection can be based on 2D/image-based object detection or 3D/shape based object detection techniques.

In some implementations, the charging station includes a locking system/feature that enables facility staff to lock or unlock specific electronic devices, specific sets of electronic devices, or all electronic devices. Example locking mechanisms include, but are not limited to, sliding/rotating metal bars, roll-top type of locking covers, fold in locks that keeps electronic devices secure, locking pins that could be above the devices or slide into cavities in any side of the devices.

The locking mechanism can secure the electronic devices and prevent unauthorized access to or damage to the electronic devices. The locking system could be located on any side or face of the charging station. The locking mechanism can include one or both of a manual operation configuration or an electronic operation configuration that uses, for example, motors and electronics. The locking system can be configured to allow for the receipt of additional electronic devices even if the charging station is locked, and electronic devices are returned late.

Figures 13A, 13B:
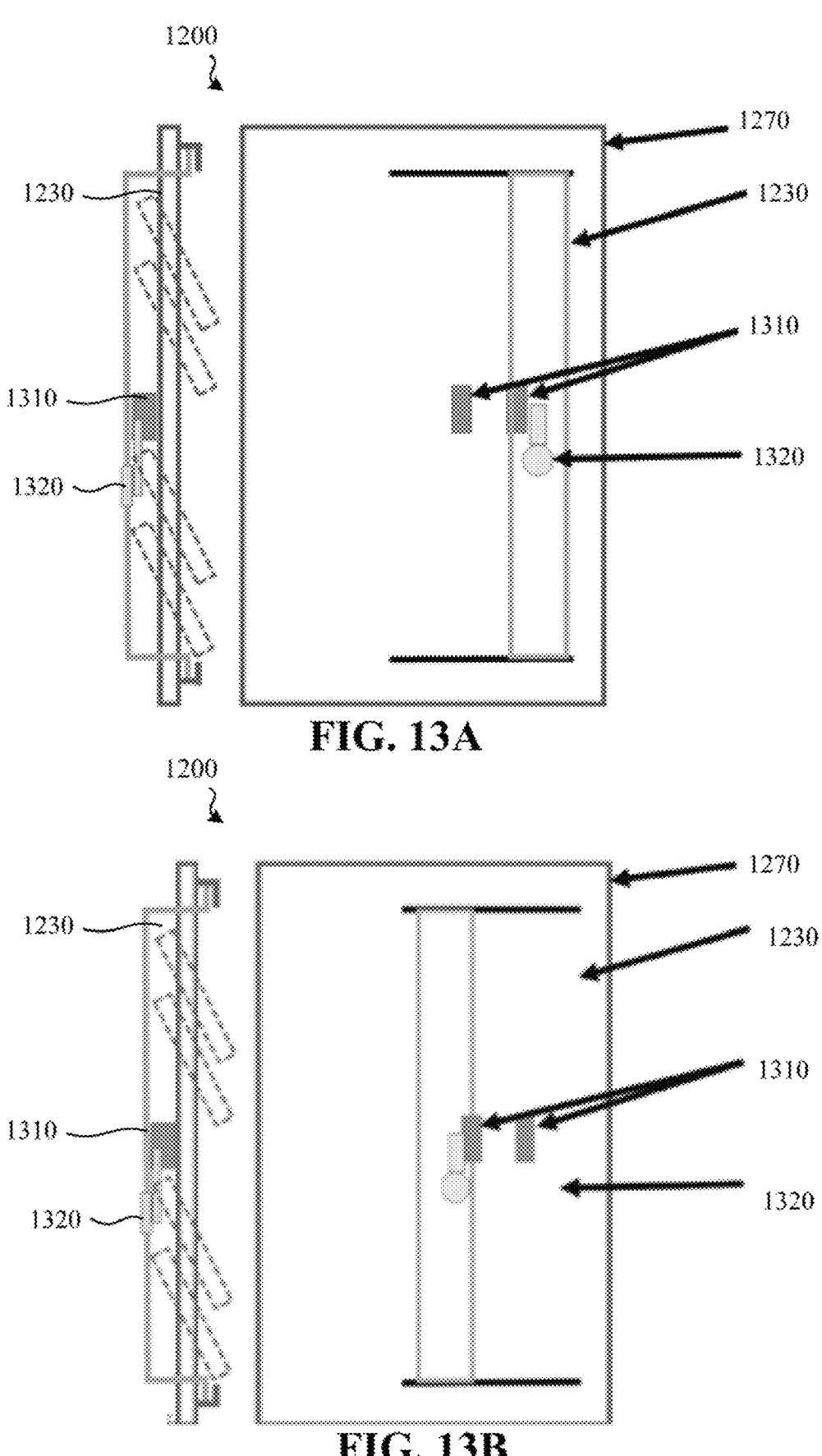
FIGS. 13A and 13B are block diagrams illustrating a locking mechanism of a charging station.
Figure 14:
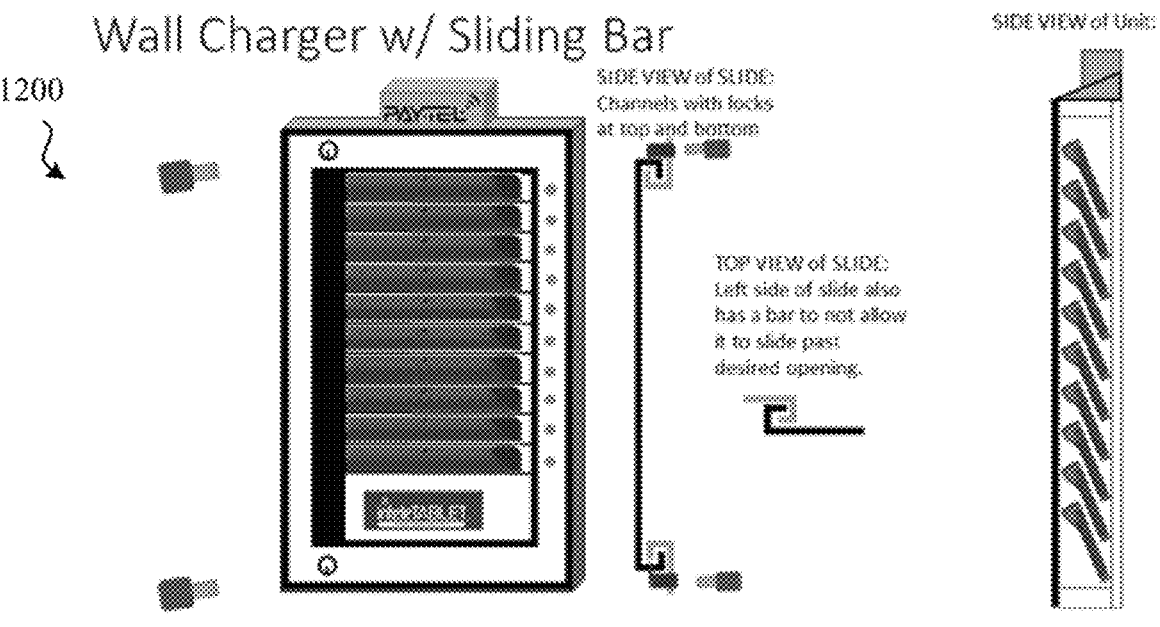
FIG. 14 is a block diagram illustrating a sliding bar locking mechanism of a charging station.

FIGS. 12, 13A, 13B, and 14 illustrate a charging station 1200 that includes slots 1210 for electronic device 1250 on fixed front panel 1270. Indicators 1240 are used to indicate charging/insertion status of the electronic devices 1250. In this example, locking bars 930 slide or rotate to secure the electronic devices 1250 within the slots 1210. In FIGS. 13A and 13B, a lock 1320 is mounted on locking bar 1230 and interacts with stops 1310. The lock 1320 will brace up against the one of the stops 1320 (e.g., the right stop) when the unit is unlocked as shown in FIG. 13A. When the unit is locked, the lock 1320 will brace up against the other of the stops 1310 (e.g., the left stop) and the locking bar 1230 would be in a more central position as shown in FIG. 13B, thus prohibiting the removal of any electronic devices.

FIGS. 15A and 15B are block diagrams illustrating locking pin-based locking mechanism of a charging station 1500. In the example of FIG. 15A, each locking pin (e.g., locking pin 1510) is configured to extend just above a respective electronic device (e.g., electronic device 1520) to prevent the electronic device from being removed when the locking pin is in a locked position. When unlocked, the locking pin 1510 is retracted (e.g., into the charging station 1500) and thus does not obstruct the electronic device 1520 from being removed.

Figures 20, 21:
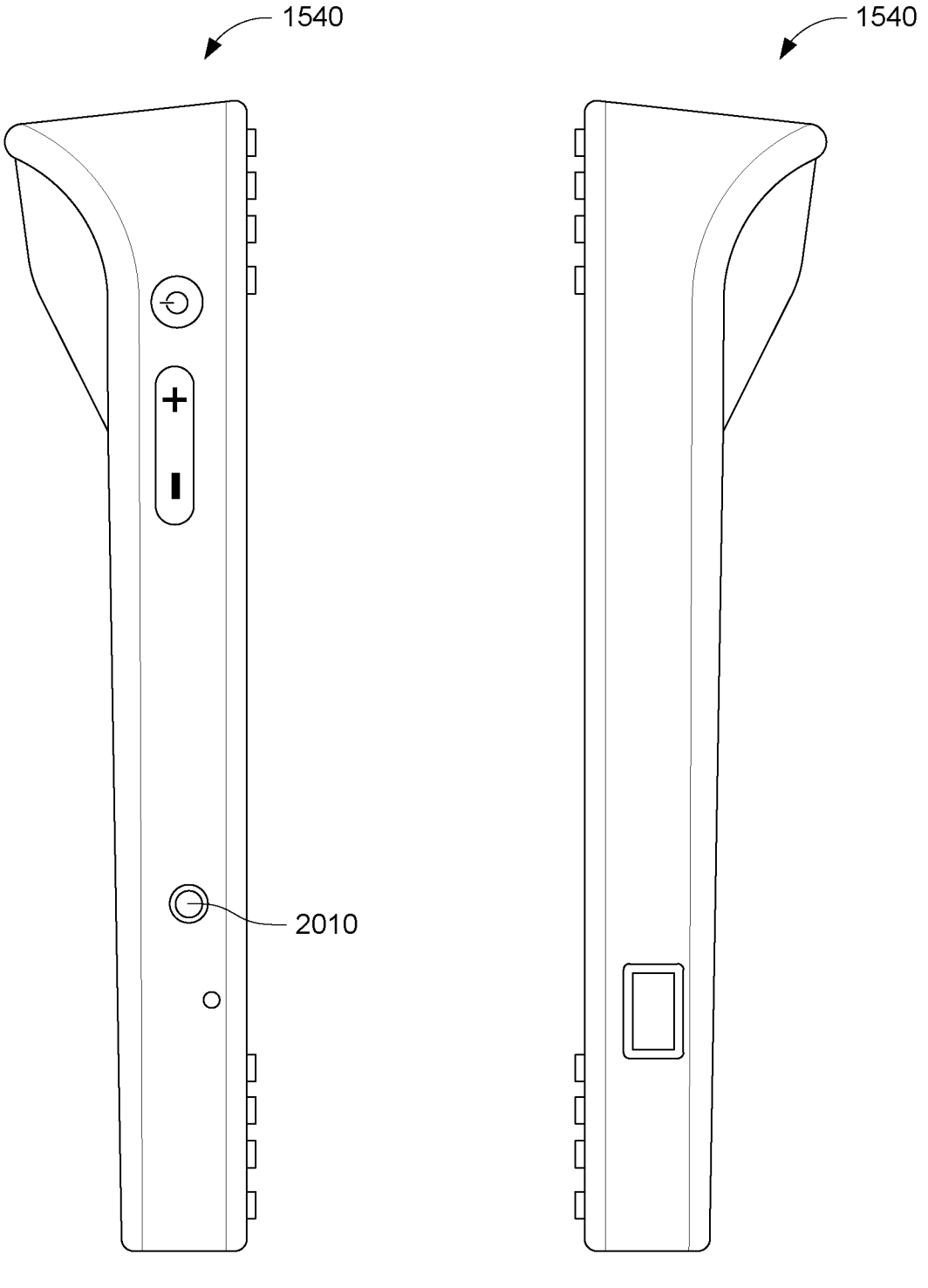
FIG. 20 is a side view of another exemplary electronic device capable of being charged via a charging station.
FIG. 21 is a side view of the electronic device of FIG. 20.

In the example of FIG. 15B, each locking pin (e.g., locking pin 1530) is configured to extend just into a side of a respective electronic device (e.g., electronic device 1540) to prevent the electronic device from being removed when the locking pin is in a locked position. For example, the locking pin 1530 could be inserted into a reinforced opening formed in an electronic device such as into reinforced opening 2010 of electronic device 1540 depicted in FIGS. 20 and 21. When unlocked, the locking pin 1510 is retracted (e.g., into the charging station 1500) and thus does not obstruct the electronic device 1520 from being removed.

Locking can be accomplished by a pin system that flips once to allow the addition of another electronic device.

In another implementation, a charging station includes a door to lock one or more of the electronic devices or for other storage purposes (e.g., usable by staff only to store their personal phones, an emergency cell phone, etc.) The locking system may provide an option to have a locking cover so no electronic devices can be accessed until allowed by service provider employee or other authorized person. A locking lever, automated lock, or other locking mechanism may be on either side of the charger as well as on the front of the charger. An additional external cover may be used to entirely cover the station to prevent access of any kind.

A charging station may be configured with various other features. A charging station may be configured to drive a remote TV, or monitor with other information. A charging station may be used as a hot spot or AP connection. A charging station may provide a data connection or store data for other electronic devices. A charging station may have other smart functions that allow communication to all the electronic devices, or from all the electronic device, with software/feature updates/special controls. A charging station may have USB and other connections to allow for data/information/services/RFID/bar code scanning/eye scan/finger print. In some implementations, the charging station receives information from the electronic devices that it charges when those devices are separated from the charging station (e.g., out in the confinement institution POD). In some implementations, information from the electronic devices is used to triangulate or otherwise determined the locations of those devices.

In some implementations, a charging station is configured to automatically connect to the electronic device when the electronic device is placed in the charging station. Plugs or wires can, but need not, be used for power or data transmission between the charging station and the electronic device. This can simplify the charging or updating of electronic devices. In some implementations, a charging station is used as a combined charger/USB/data device that can charge multiple tablets (or other electronic devices) and connect with the electronic devices to do updates, uploads, and other data-intensive data transfers.

In some implementations, a charging station is configured to charge multiple devices of different types, e.g., both tablets and laptops, both tablets and mobile phones, etc., or devices of a same type but of different sizes, e.g., tablets with 8 inch screens and tablets with 10 inch screens, etc.

In some implementations, one of the electronic devices in the charging unit is in a fixed position/not removable and can only be used for specific functions (i.e., ordering commissary, video calls, etc.). Such a device can provide an interface for the charging station monitoring and management functions. In other implementations, any of the electronic devices, given proper authorized user authorization, can be used as an input/output interface for the charging station monitoring and management functions.

In some implementations, a charging station has a handset, speaker, or display for general user features such as staff announcements, music, video, time display, etc. A charging station could support ADA requirements by allowing video relay services through it for the hearing impaired. In some implementations, an ear bud or other listening device is attached to a charging station and the inmates are enabled to perform calls or video calls using the charger. A charging station may have a microphone that allows an inmate to call for help, for example, responding automatically to particular words ("help," "guard," "fire,") etc.

In some implementations, a charging station includes ruggedized components, e.g., components that include rubber or shock absorbing surfaces or reinforced components.

A charging station may have slanted side vents, no vents on the top, louvers added to the vents, drain holes in the bottom of the charging station, and/or other features that facilitate venting while prohibiting fluid entry. In some implementations, a charging station includes a vapor barrier at the back to prohibit the entry of moisture from behind the charging station.

In some implementations, a charging station includes a battery backup. If the electricity goes out, the battery on the charging station can act like a UPS and an indicator light can provide emergency lighting to the POD or other confinement facility area. Similarly, a charging station can be configured with connectivity to the electronic devices even in power outage circumstances to ensure that calls/messaging/communications can continue when the power is out. In another example, the charging station may be configured to send notifications to the inmates during a power out emergency.

In some implementations, the charging station has a slanted or sloped top or cap (see, for example, the side views in FIGS. 14 and 15) to prevent or discourage inmates from placing drinks on top of the charging stations. The slanted or sloped top can be part of the charging station body or be provided by a cap or other add-on component. The slope on the top of the charging station can prevent or discourage inmates from putting things on top of the charging station that contain liquids, small objects, or other undesirable substances and thus reduce the risk of damage to the internal parts of the charging station. The charging station may have channels that would allow liquids and small objects to pass through the charging bays/slots and a sloped top may reduce the risk of such intrusions. In other implementations, the top of the charging station has alternative geometries (e.g., curved) other than horizontal to prevent or discourage inmates from resting objects on top.

In some implementations, a charging station includes antibacterial lights positioned to illuminate one or more of the electronic devices during charging or otherwise while the electronic devices are inserted within the charging station. In one example, the charging station includes a germicidal lamp that produces ultraviolet light.

The short-wave ultraviolet light disrupts DNA base pairing causing formation of pyrimidine dimers and lead to the inactivation of bacteria, viruses, and protozoa.

In some implementations, the charging station includes one or more indicators. For example, the charging station may be configured to trigger an alarm based on detecting an intrusion. In some implementations, the charging station includes an indicator (e.g., light, speaker, etc.) that provides an audible or visual indication when a device has been seated correctly or correctly locked. In some implementations, the charging station includes an alarm that is triggered when an attempt is detected to remove an electronic device during restricted times or when the electronic device is locked at the charging station.

In some implementations, the charging station is configured to lock or otherwise prevent removal of an electronic device unless the electronic device is charged to a particular degree, e.g., 75% charged, fully charged, etc. Similarly, removal of the electronic device may be prevented while the electronic device is receiving updates or when an electronic device fault or error has been detected.

In some implementations, the charging station is configured to assess the status or condition of an electronic device when the electronic device is returned. For example, the charging station may run a diagnostic on a returned electronic device capture an image of the returned electronic device and analyze the image to identify damage (e.g., broken screens, etc.), or otherwise assess the status or condition of the electronic device. In one example, an image of the device is captured when the device is checked out or removed and compared with an image of the device when the device is checked in or returned.

In some implementations, user-specific data and use history on each of the electronic devices is automatically erased when the electronic device is checked in or returned to the charging station. In some implementations, a copy of user-specific data is captured and stored on a server or other storage device for later use by the particular user or review by officers, investigators, law enforcement, or other persons.

In some implementations, the charging station is part of a system that facilitates management of electronic devices. In one implementation, the system receives an inmate identifier and a device identifier when the inmate removes a device from the charging station. For example, the inmate may enter an inmate ID and password or otherwise provide login/identification credentials. The charging station may track the removal of a particular device, e.g., based on tracking which devices are in which slot or based on communicating with the electronic device that is removed.

When an inmate returns a tablet or other electronic device to the charging station, the system again recognizes the event. For example, the charging station may identify the particular electronic device that is returned to the charging station based on communicating with the electronic device or using information provided by the inmate, or both. Accordingly, at any given time, e.g., at the end of the day, facility officers are able to access the system to determine which inmates still have electronic devices outstanding and identify any missing electronic devices without having to perform manual inspections. The system replaces the error prone and burdensome manual tracking processes that would otherwise be required with an efficient and accurate automated electronic device tracking process.

The charging station may be configured to send wireless communications to the electronic devices to cause the electronic devices to discontinue operation and/or to present messages. In some implementations, device usage is restricted to particular hours, e.g., until 8 μm, and a message is sent to electronic devices at or before the end of the usage period instructing the inmates to return the electronic devices to the charging station. In some implementations, a message is sent to a particular electronic device or particular group of electronic devices to inform the respective users of a particular message. For example, all devices checkout out to inmates in a particular POD may receive a message that lunch is starting.

Exemplary Device Management and Localization

Some implementations provide systems and methods for managed inmate device charging, battery-aware usability control, and/or device localization within confinement institutions. Various techniques may be used to provide device management in controlled environments, and more specifically to provide for monitoring, managing, and locating inmate devices, such as tablets, in confinement institutions. The technology may integrate mobile device management (MDM), charging station status, battery-aware usability control, and localization features to reduce loss, theft, damage, and misplacement of inmate devices while providing actionable visibility to staff.

Confinement institutions may deploy individualized and/or shared mobile devices, such as tablets, for inmate use. Loss, theft, damage, and failure to return devices to chargers at the end of a session create operational burdens and costs. Conventional solutions often rely on physical locking mechanisms, manual check-in/check-out processes, or identification techniques that are fragile or impractical. Moreover, facilities commonly lack real-time visibility into which device is checked out, by whom, and whether the device is charging or nearing depletion. When a device goes offline for an extended period, staff may only learn days later that multiple devices are missing or unreturned, by which time the devices may be unrecoverable. Facilities may employ deterrents by denying subsequent access if devices are not returned.

Inmate devices may be controllably, physically locked into a charging station and/or disabled in various circumstances. In some implementations, a charging station is configured to give access to (e.g., unlock, enable, etc.) one of multiple physically locked and/or disabled tablets to an inmate when the inmate requests a tabled. The inmate may provide credentials (e.g., entering a code on a user interface of the charging station or other device) and, in response, the charging station may unlock a particular tablet, e.g., a tablet having the highest amount of current charge. In another example, an inmate is enabled to check in and out a tabled using biometric information, e.g., facial recognition, iris recognition, fingerprint recognition, etc. The inmate may provide such biometric information by complying with instructions regarding where to stand, position their head, position their finger tip, etc. and the device may capture data, e.g., images of the face, images of the eye, a scan of a fingertip, etc., and, in response to verification inmate identity and/or authorization, the charging station may unlock a particular tablet, e.g., a tablet having the highest amount of current charge.

Various implementations disclosed herein provide an integrated approach that: (i) monitors charging status and check-in/check-out events; (ii) tracks battery levels; (iii) proactively disables inmate-facing functionality as battery thresholds are met while preserving power for localization and communications; (iv) enables staff to quickly find devices using audio/visual cues and location data; and (v) presents an intuitive, real-time display of device status to staff, via a television or staff-operated device.

Some implementations provide systems and methods for managing inmate devices within a confinement institution. At a computing device comprising a processor, a system determines that an inmate device has been removed from a charging station that serves multiple devices. The system monitors remaining battery power and, upon detecting that remaining power satisfies a condition (e.g., drops below a threshold), disables user-interface functionality on the device to render it unusable by the inmate while continuing to power a localization function capable of providing information that enables staff to locate the device. The localization function can respond to requests from a staff-operated locating device by emitting an audio signal or displaying a visual signal to identify the device's location. The system can further send an electronic communication that the device has met the condition and has not been returned, optionally identifying the last user or the user who removed the device.

A monitoring system may aggregate status information for inmate devices, including check-in/check-out events, charging station associations, battery levels, and last-user identity information. A listing interface may graphically display device statuses—e.g., via a television mounted above the charging station or a handheld staff device-clearly distinguishing devices that have both been removed from the charger and have remaining battery power that satisfies the condition. The interface can display last checkout times, last users, charger identifiers, and battery state, enabling staff to take immediate action. The approach may help reduce loss and search time by coupling battery-aware usability control with persistent localization and a real-time status display. The approach may be integrated with existing MDM platforms that track device telemetry and usage and provides policies that can incentivize timely returns (e.g., privileges when compliance is high, limiting access when devices are not returned), without necessarily requiring per-device physical locks. The display of the status of each device can be controlled via a specialized program that controls the tablets as well. An area that can not support a TV, or that does not have staff availability for continuous monitoring may be provided with a report, e.g., each morning or at a specific time at night, telling them that a particular area, e.g., POD A, has one or more particular devices (e.g., tablet serial number 1234) not in a charger or missing for a specified time.

In some implementations, a confinement institution environment includes a plurality of inmate devices (e.g., tablets) and one or more charging stations configured to concurrently charge multiple devices. In some implementations, charging stations incorporate a locking bar configured to secure multiple devices collectively, rather than relying on individual locks per device. Each charging station may have a unique charger identifier (e.g., a serial number) that is communicated to inmate devices when docked and recorded by a management system to associate devices with specific stations.

A mobile device management (MDM) component may monitor device telemetry and state, including charging status, battery level, network connectivity, last user identity, and check-in/check-out events. The MDM communicates with an on-premises or cloud-based management server. A device localization subsystem resides on the inmate device and remains powered even when inmate-facing user-interface functionality is disabled, enabling audible or visual signals to assist staff in finding devices. Staff may operate a locating device (e.g., a tablet, phone, or kiosk) that can query or command inmate devices to emit location cues, receive device state updates, and display a consolidated status listing.

When an inmate device is docked in a charging station, the device detects charging state and may read or otherwise confirm the charger identifier. The MDM records a check-in event including device ID, charger ID, timestamp, battery state-of-charge, and optionally the identity of the last user. When the device is removed from the charging station, the device and/or MDM records a checkout event including time of removal and user identity (e.g., the user who authenticated to the device around the time of removal). Associations between device and charger may be used to verify return location and to show a device's expected slot to staff and/or inmates. A camera for inmate identification can be on the charger (e.g., built in or mounted on device), or mounted above or in another area. Additionally or alternatively, a camera on the tablet may be used for sign on/off and/or taking pictures to identify who is using it and/or the location of the device at certain times and/or events.

In some embodiments, device identifiers are presented on the back of the device to assist users in finding their assigned device. Facilities may use temporary markings (e.g., the last three digits of a serial number written with a white marker) to facilitate identification. Such markings can be changed or removed as needed without modifying the device chassis permanently, providing flexibility during repairs or reassignment. Such markings may be printed on the devices using a process that is easy to perform within the confinement institution, e.g., via a marking device that provides ink, paint, etc. to provide markings on the devices. Additionally or alternatively, the inside of tablets may be treated (e.g., sprayed) with an ultraviolet paint that would get on the inmates' hands, etc. if the tablet was opened or disassembled, e.g., for unauthorized access to the battery. Then an officer or other institution official could walk around with an ultraviolet light to detect if ink is present on hands, clothing, or walls, etc. Chemicals visible under blacklight could similarly be used.

Each inmate device may be configured to continuously monitor battery state-of-charge and/or predict remaining runtime. The system may evaluate whether remaining battery power satisfies a condition, such as falling below a threshold percentage, below a time-to-empty value, or meeting a composite policy that accounts for device usage, scheduled return windows, and facility rules.

Upon determining that the condition is satisfied, the device disables the inmate-facing user-interface functionality, rendering the device unusable for inmate tasks while preserving sufficient power to operate the localization function and communications sufficient to coordinate with staff. The device may present an indication that it is effectively out of power for user purposes and instruct the user to return the device to the charging station. Internally, the device enters a low-power mode that maintains essential services, such as periodic beaconing, receipt of locate commands, and emission of audio or visual signals.

The UI-disabled state may persist until the device is returned to the charging station and charging resumes, at which point inmate-facing functionality can be re-enabled and normal use restored (e.g., for the same or another inmate to use at a later checkout event). This approach ensures that devices are not fully depleted, enabling a localization function, e.g., enabling staff to trigger an audio "find" tone or visual display or to locate the device based on communications with the management system. In some embodiments, the device may enforce progressive limitations (e.g., restricting content access or network features as the threshold approaches) and then disable UI upon threshold crossing.

The localization function provides information that enables staff to locate the inmate device within the confinement institution. This may include one or more of:

emitting an audio signal at a volume and cadence designed to be heard within typical confinement facility cell block or other area;

displaying a distinctive visual signal (e.g., flashing screen, LED, or on-screen message) to aid visual identification;

responding to commands from a staff locating device via the MDM or a local network; and/or sending an electronic communication indicating that the device has met the condition, has not been returned, and optionally identifying the last user and/or the user who removed the device from the charger.

Localization may rely on device-to-device awareness (e.g., nearby devices detecting each other over short-range communications when they remain docked and powered), association with charger identifiers, timestamps of removal, and user authentication records. The device can also store or communicate the last known charger identifier, last connected network, and most recent activity. Staff can query the device and trigger audio/visual signals to quickly locate it.

A monitoring system may collects status information for inmate devices, including:

check-in/check-out events relative to charging stations, with timestamps and charger identifiers;

remaining battery power and expected time to threshold;

current usability state (e.g., active, approaching threshold, UI disabled);

last user identity associated with the device and optionally the user who removed the device from the charger; and/or whether the device is charging, disconnected, or offline.

A graphical listing interface may be provide to present information about device location (e.g., in charger, out of charger, with a particular inmate, out of service, etc.). A graphical information interface may provide specific information about at least a subset of devices, visually distinguishes devices that have been removed from the charging station and have remaining battery power satisfying a condition (e.g., remaining power below a threshold power level). For example, devices requiring action may be presented in red, devices currently charging may be presented in yellow, and devices recently removed but above the threshold may be presented in orange. The listing may also display last checkout times, last users, charger IDs, and battery levels.

In one embodiment, the listing is displayed on a television mounted above the charging station, providing immediate visibility to staff and inmates. In other embodiments, the listing is displayed on a staff-operated localization device, such as a tablet or phone, allowing staff to view and act upon device statuses in areas where a television cannot be installed. The interface may allow staff to select a device and issue a "find" command, causing the device to emit audio or visual signals. The interface may also support policy-based actions such as limiting device features when devices are not returned, or triggering incentives when devices are consistently returned on time.

Facilities may configure policies that provide positive incentives for timely device return (e.g., granting privileges when compliance rates exceed a threshold) and impose deterrents when devices are not returned (e.g., restricting device features or access for a subsequent period). Policies can be enforced via the MDM by adjusting device capabilities, disabling certain applications, or limiting network access. The combination of visibility, localization, and policy controls enables facilities to manage device return behavior effectively.

The system may leverage existing MDM platforms that provide telemetry, application control, user association, and remote command capabilities for mobile devices. The localization function can be implemented as part of an MDM-managed application or service that remains powered in the UI-disabled state. The MDM can:

track device battery levels and charging status;

record user authentication events and associate users with devices;

issue commands to disable UI, present return instructions, and trigger localization signals;

receive device communications indicating threshold events and non-return status; and/or populate the status listing interface for display to staff.

Inmate devices may be standard tablets configured for institutional use. The devices run an operating system with a power management module, an MDM agent, and a localization service. When the battery threshold is met, the power management module transitions the device to a UI-disabled mode, ensuring that sufficient power remains for localization and communications. The localization service maintains connectivity with the MDM (subject to available network) and responds to locate commands by emitting audio or visual cues.

Charging stations provide physical slots for multiple devices and can include a locking bar to secure devices collectively. The stations may expose charger identifiers to docked devices via a barcode, QR code, NFC, or via software association when docked. The charger identifier is recorded in the MDM to associate device state with a specific station.

The management server aggregates telemetry via secure communications. The status display interface can be implemented as a web application rendered on a television-connected device, a native application, or an MDM dashboard view. The staff locating device can issue locate commands and receive device responses, even when the inmate device's UI is disabled.

To ensure that localization remains available, the system reserves a portion of battery capacity for low-power localization when the threshold is met. The device shuts down high-consumption processes and renders inmate-facing functions unusable. The localization service operates in a low-power mode, enabling periodic beaconing or responding to locate commands. The device may emit a periodic tone or flashing visual signal, with timing calibrated to preserve remaining power while assisting staff in location. When the device is returned to the charger, normal functionality resumes automatically.

The following exemplary operations may be performed by the system:

1. Detection of removal and battery monitoring. The device is removed from the charging station, triggers a checkout event, and associates the last authenticated user. The MDM monitors battery levels.
2. Threshold crossing and UI disable. As battery falls below a configured threshold, the device disables UI and displays or announces return instructions. The device enters low-power mode, preserving power for localization and communications.
3. Staff notification and localization. The device sends an electronic communication to the management server or staff locating device indicating threshold met and non-return, optionally including last user identity and removal time. Staff selects the device on the listing interface and issues a locate command. The device emits an audio signal or visual signal and can be found promptly.
4. Return and reset. Upon return to the charging station, the device detects charging, logs a check-in event with charger ID and timestamp, re-enables UI, and resumes normal operation.

The condition used to trigger UI disable may be based on battery percentage, estimated time-to-empty, predicted time until required return, or a composite metric. Localization may use audio signals, on-screen messages, LED indicators, or other cues. The listing interface may be displayed on various devices, including televisions mounted above charging stations, wall-mounted panels, tablets, or phones operated by staff. User identity may be captured via device authentication records, kiosk login, or charger-based workflows. The system is applicable to tablets and other inmate devices that support MDM and power management.

In some implementations, additional identification methods (e.g., temporary markings such as writing the last three digits of the serial number) may be used to facilitate inmate device assignment. Such markings can be removed or updated as devices are repaired or reassigned. RFID may be employed in certain configurations; however, the system's MDM-based telemetry and localization functions provide immediate visibility and findability without relying solely on RFID range or presence detection.

The disclosed systems and methods reduce loss and search time by ensuring that devices remain locatable even when inmate-facing functions are disabled. They provide real-time visibility into device check-in/check-out status, battery levels, and user associations. Facilities can configure incentives and deterrents to drive timely returns. The approach leverages widely available MDM features, reduces reliance on per-device physical locking, and adapts to varied physical layouts through television displays or staff-operated locating devices.

The system may include configurable thresholds with hysteresis to prevent frequent toggling around the threshold; secure communications and access controls to protect inmate and staff data; logging and audit trails for device movement and policy enforcement; and robust handling of edge cases, such as devices temporarily losing network connectivity or temporarily entering offline states. The localization function may include fallback cues that do not require network connectivity once triggered. Devices and management servers can be updated via over-the-air updates to refine thresholds and localization behaviors.

The disclosed systems and methods combine battery-aware usability control, persistent localization capability, and real-time status displays to improve management of inmate devices in confinement institutions. By leveraging MDM telemetry and policy enforcement, the system ensures that devices remain locatable when battery thresholds are met, reduces search time and loss, and provides staff with actionable, intuitive visibility into device status and user associations.

Some implementations provide multiple charging stations that can be connected to one another (e.g., physically and electrically) to provide easily scalable multi-device charging. For example, each charging station can be configured to charge 10 devices. One charging station can be used to charge 10 electronic devices, two connected charging stations can be connected to charge 20 electronic devices, three connected charging stations can be connected to charge 30 electronic devices, etc. The first charging station electrically plugs into a power outlet or is hardwired to an intra-wall electrical wire via a wall opening behind the charging station (e.g., through a hole in the wall). The additional charging stations plug into the first charging station or one another (e.g., in a chain configuration, a hub and spoke configuration, etc.) or directly to an outlet or intra-wall connection. In some implementations, multiple charging stations are connected via a hidden conduit between the units.

In some implementations, the charging station includes an outer case that protects the electronic devices from access and damage. The outer case may be configured to be entirely removed, partially removed, or moved to expose the electronic devices for access by the inmates and other users. Such an outer case may include a sliding portion (see FIG. 6 for examples of a sliding portions on mobile charging station units) or a hinged portion that allows the outer case to move to expose the electronic devices for access and return. In one example, hinges connect an outer case to a body of the charging station, e.g., configured to allow the outer case to be raised and lowered.

Exemplary Electronic Devices

FIGS. 16-19 illustrate an exemplary electronic device configured for use with a charging station and/or in a confinement institution. The example electronic device 1600 is configured to be oriented at an angle relative to a flat surface upon which it is rested. The bump portion 1710 is shaped such that, when the electronic device 1600 is laid face up, i.e., with its underside resting on a horizontal underlying surface, the bump portion 1710 will cause the device screen to sit at a non-horizontal angle. The screen will be tilted up to enable easier viewing by an inmate or other user, without requiring the inmate/user to hold the device at such an angle. The bump portion, in some implementations, thus serves to both ensure proper insertion/alignment in the charging station and facilitate a better resting display angle for the electronic device.

Numerous specific details are set forth herein to provide a thorough understanding of the claimed subject matter. However, those skilled in the art will understand that the claimed subject matter may be practiced without these specific details. In other instances, methods apparatuses, or systems that would be by one of ordinary skill have not been described in detail so as not to obscure claimed subject matter.

Unless specifically stated otherwise, it is appreciated that throughout this specification discussions utilizing the terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied for example, blocks can be re-ordered, combined, or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" or "comprising," when used in this specification, specify the presence of stated features, integers, steps, operations, elements, or components, but do not preclude the presence or addition of one or more other features, integers, steps, operations, elements, components, or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description and summary of the disclosure are to be understood as being in every respect illustrative and exemplary, but not restrictive, and the scope of the disclosure disclosed herein is not to be determined only from the detailed description of illustrative implementations but according to the full breadth permitted by patent laws. It is to be understood that the implementations shown and described herein are only illustrative of the principles of the present disclosure and that various modifications may be implemented by those skilled in the art without departing from the scope and spirit of the disclosure.

What is claimed is:

1. A method comprising:
    at a computing device comprising a processor:
        determining that an inmate device has been removed from a charging station provided for charging a plurality of inmate devices within a confinement institution;
        determining that remaining battery power available on the inmate device satisfies a condition;
        based on determining that the remaining battery power available on the inmate device satisfies a condition, disabling user-interface functionality on the inmate device and continuing to power a localization function on the inmate device, wherein the localization function provides information that enables localization of the inmate device; and
        locating the inmate device within the confinement institution based on the information provided via the localization function.

2. The method of claim 1, wherein disabling the user-interface functionality further comprises providing an indication that the inmate device is out of power.

3. The method of claim 1, wherein the inmate device is unusable while the user-interface functionality is disabled.

4. The method of claim 1, wherein the user-interface functionality is disabled until the inmate device is returned to the charging station.

5. The method of claim 1 further comprising, based on determining that the remaining battery power available on the inmate device satisfies the condition, providing an indication on the inmate device instructing a user to return the inmate device to the charging station.

6. The method of claim 1, wherein the localization function on the inmate device provides an audio signal or displayed signal useable to identify the location of the inmate device.

7. The method of claim 1, wherein the localization function on the inmate device responds to a request from a locating device by providing an audio signal or displayed signal useable to identify the location of the inmate device.

8. The method of claim 1, wherein the localization function on the inmate device sends an electronic communication to a locating device informing the locating device that the inmate device has satisfied the condition and has not been returned to the charging station.

9. The method of claim 8, wherein the electronic communication identifies a user who was last using the inmate device.

10. The method of claim 8, wherein the electronic communication identifies a user who last removed the inmate device from the charging station.

11. The method of claim 1, wherein the inmate device is a tablet.

12. The method of claim 1, wherein the condition is that remaining battery power available is less than a threshold.

13. The method of claim 1, wherein the localization function is part of a mobile device management (MDM) system that provides communication information tracked on the inmate device to a separate localization device.

* * * * *